US012692467B2

(12) United States Patent
Lee et al.

(10) Patent No.: US 12,692,467 B2
(45) Date of Patent: Jul. 28, 2026

(54) HIGH-THROUGHPUT MAGNETIC ACTUATION PLATFORM FOR CANCER TREATMENT SCREENING

(71) Applicant: Purdue Research Foundation, West Lafayette, IN (US)

(72) Inventors: Hyowon Lee, West Lafayette, IN (US); Hyunsu Park, West Lafayette, IN (US); Luis Solorio, West Lafayette, IN (US); Angel Enriquez, West Lafayette, IN (US); Sarah Libring, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 836 days.

(21) Appl. No.: 16/936,119

(22) Filed: Jul. 22, 2020

(65) Prior Publication Data

US 2021/0040427 A1 Feb. 11, 2021

Related U.S. Application Data

(60) Provisional application No. 62/877,694, filed on Jul. 23, 2019.

(51) Int. Cl.
| | |
|---|---|
| *C12M 1/32* | (2006.01) |
| *C12M 1/12* | (2006.01) |
| *C12M 1/36* | (2006.01) |
| *C12M 1/42* | (2006.01) |
| *C12M 3/00* | (2006.01) |
| *C12N 5/00* | (2006.01) |
| *C12N 5/071* | (2010.01) |

(52) U.S. Cl.
CPC ............ *C12M 23/12* (2013.01); *C12M 23/44* (2013.01); *C12M 25/14* (2013.01); *C12M 35/06* (2013.01); *C12M 41/48* (2013.01); *C12N 5/0062* (2013.01); *C12N 5/0697* (2013.01)

(58) Field of Classification Search
None
See application file for complete search history.

(56) References Cited

U.S. PATENT DOCUMENTS

2017/0101628 A1* 4/2017 Ingber .................. C12M 25/02

OTHER PUBLICATIONS

Cui et al., Nat. Commun. 6: 6333 (2015).*
Matsui et al., PLoS ONE 13(9): e0203448 (2018).*
Kamble et al., Micromachines 8: 256 (2017).*
Willerth et al., StemJournal 1: 1-25 (2019).*
Ciu, 2015, Cyclic stretching of soft substrates induces spreading and growth, Nat Commun 6:6333, 8 pages.
Gudipaty, 2017, Mechanical stretch triggers rapid epithelial cell division through Piezo 1, Nature , 543(7643):118-121.

(Continued)

*Primary Examiner* — Erin M. Bowers
(74) *Attorney, Agent, or Firm* — Brown Rudnick LLP; Adam M. Schoen

(57) ABSTRACT

Cell-culture platforms are described that can impart cyclic strain on a biologically-relevant culture substrate. Accordingly, systems and methods of the invention can provide a more accurate model of physiological strain and forces than earlier technologies. Systems of the invention enable high-throughput experimentation in standard culturing equipment, while utilizing a 3D physiologically-relevant environment.

4 Claims, 21 Drawing Sheets

(56)     References Cited

OTHER PUBLICATIONS

Wang, 2018, Arterial Wall Stress Induces Phenotypic Switching of Arterial Smooth Muscle Cells in Vascular Remodeling by Activating the YAP/TAZ Signaling Pathway, Cell Physiol Biochem 51(2):842-853.

Yadav,2019,Stretching cells—An approach for early cancer diagnosis, Exp. Cell Res., 378(2):191-197.

Yadav, 2020, Stretching Induces Overexpression of RhoA and Rac1 GTPases in Breast Cancer Cells, Advanced Biosystems, 4(2)1900222.

* cited by examiner

PDMS

FIG. 5A
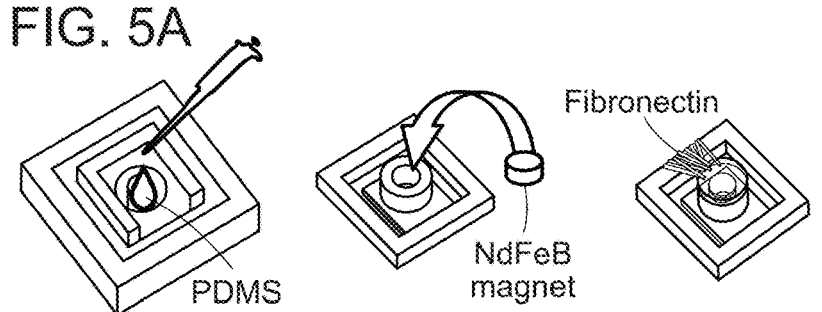
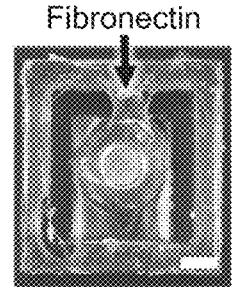
FIG. 5B
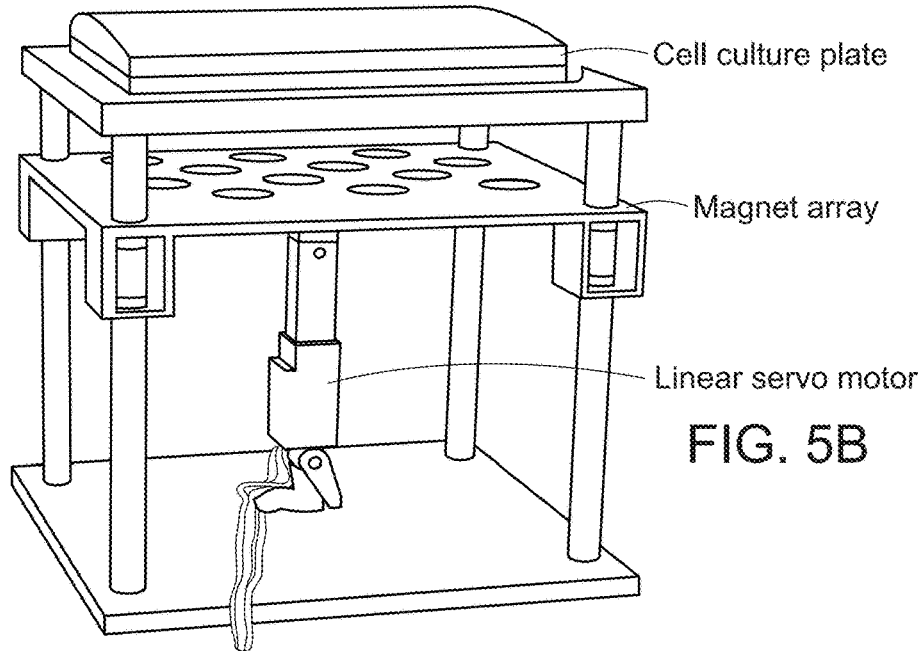
Cell culture plate
Magnet array
Linear servo motor
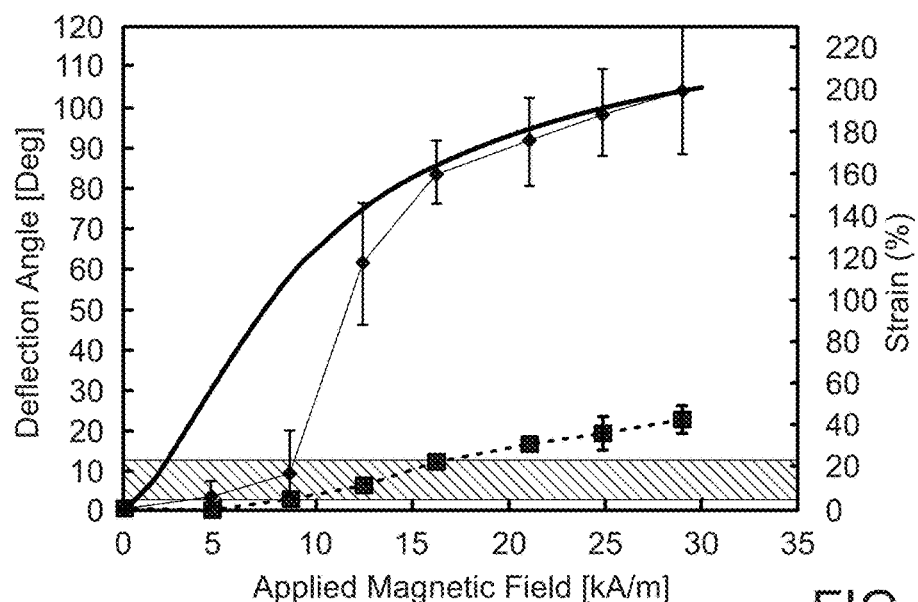
FIG. 5C FIG. 5D
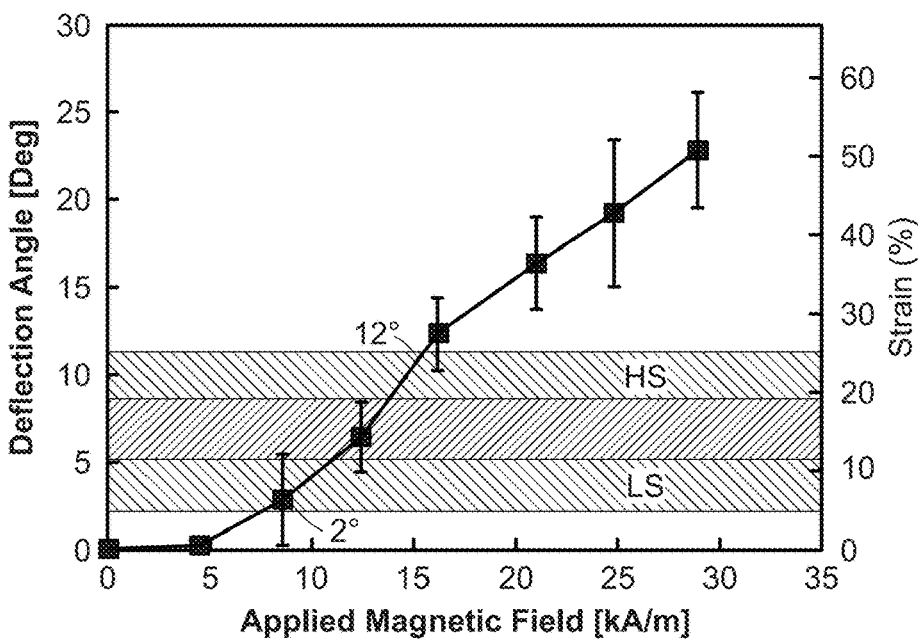
FIG. 5E
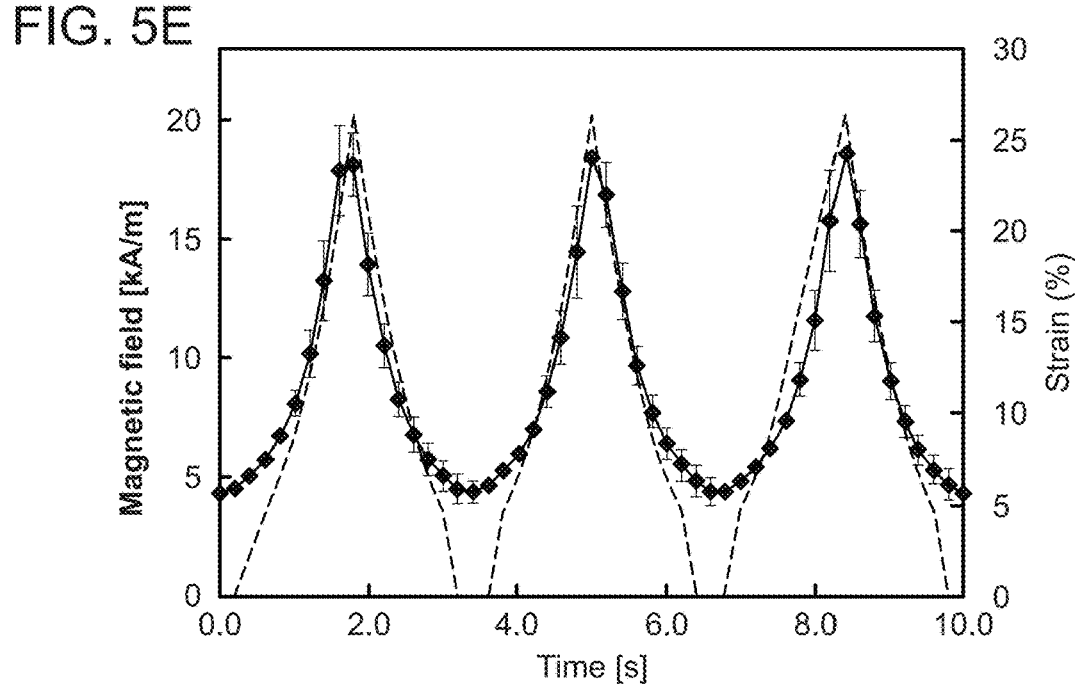
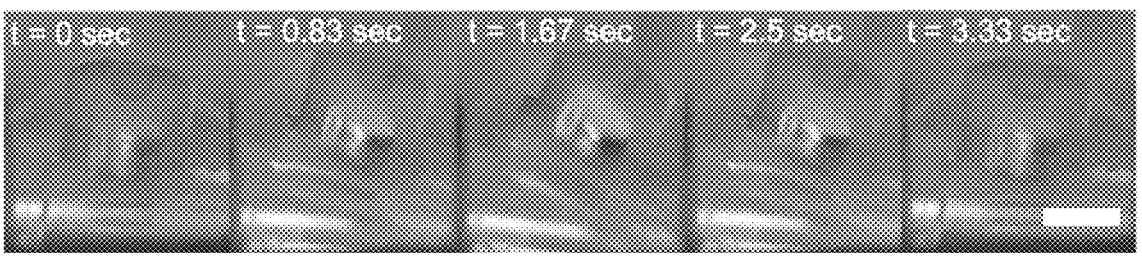
FIG. 5F

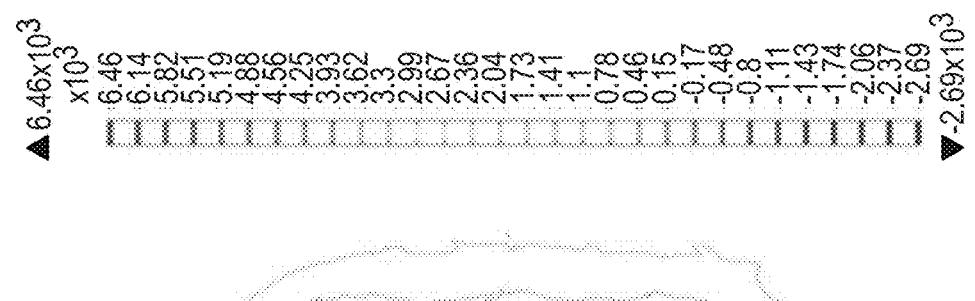
FIG. 9B
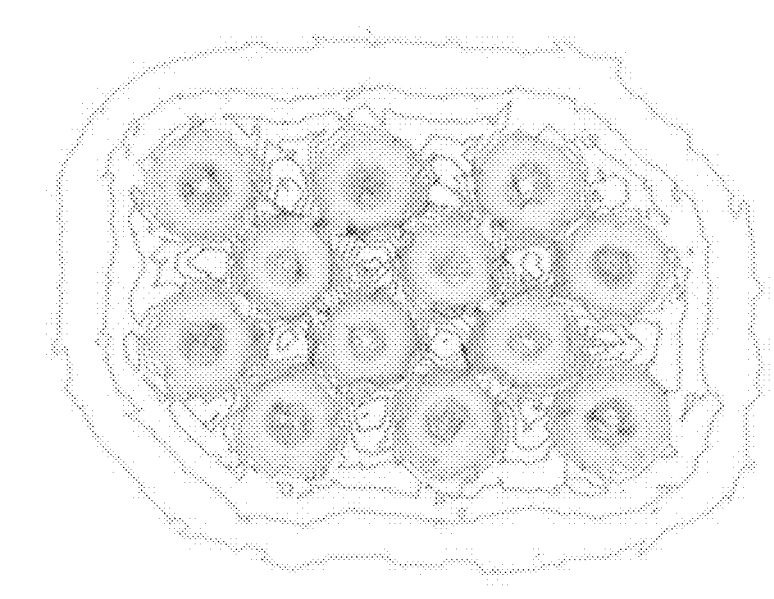
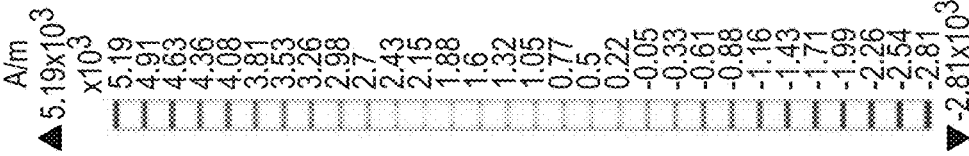
FIG. 9A
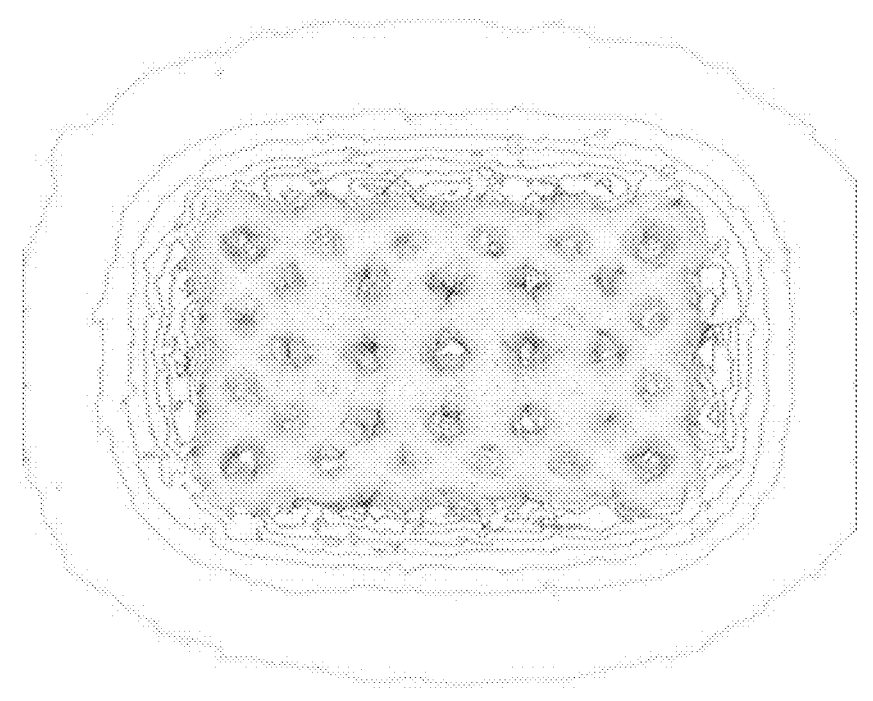

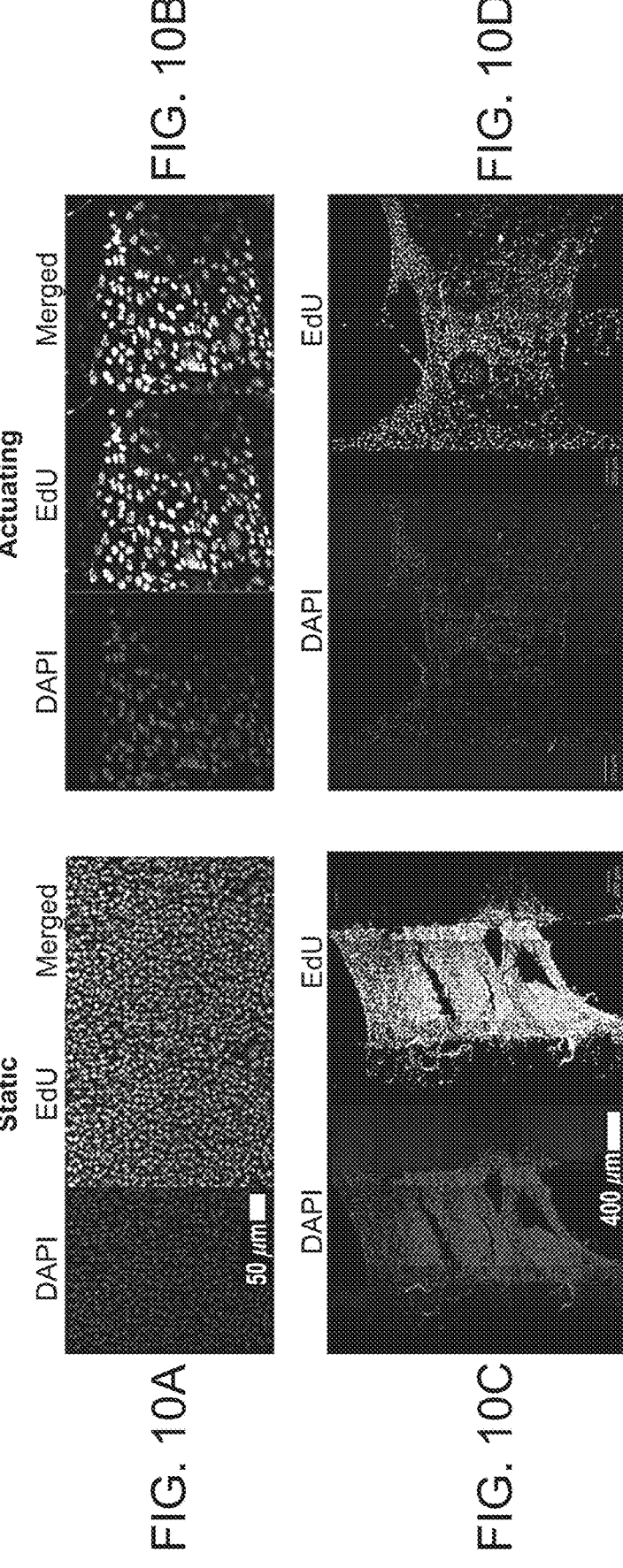

HIGH-THROUGHPUT MAGNETIC ACTUATION PLATFORM FOR CANCER TREATMENT SCREENING

RELATED APPLICATIONS

This application claims the benefit of and priority to U.S. Provisional Patent Application Ser. Nos. 62/877,694, filed Jul. 23, 2019, the content of which is incorporated herein in its entirety.

TECHNICAL FIELD

This Application relates to platforms for evaluating the impact of mechanical cues on cancer cell differentiation and treatment.

BACKGROUND

Breast cancer is the most frequently diagnosed cancer among females, with an incident rate of over 1.6 million cases per year worldwide. The five-year survival rate is exceptional if the dis-ease remains local, but quickly drops once the tumor has metastasized. Only approximately 5%-10% of patients with metastatic breast cancer survive more than 5 years, and only 2%-5% survive more than 10 years. Across all solid-tumor cancers, metastasis is responsible for approximately 90% of cancer-related deaths. In addition, recent research has shown that breast cancer cells disseminate early in the disease but remain dormant for 10+ years before reactivating and becoming clinically detectable. Specifically, between 2001 and 2007, 60% of patients diagnosed with breast cancer had no locoregional or metastatic signs. However, approximately 30% of these locally-confined patients will eventually relapse with secondary tumors. It has been shown that approximately 33% of women diagnosed with breast tumors only 4 mm in size already house disseminated cancer cells. As such, breast cancer is no longer considered a curable disease. It is classified as a chronic disease that can recur after 10-30+ years. The mechanical forces at some of the most common metastatic sites, the bones and lungs, likely significantly impact breast cancer cell behavior, just as mechanical properties (e.g. stiffness) in the primary tissue have been shown to affect disease progression and metastatic potential.

Previous research has indicated that induced stromal stiffening at the primary tumor site helps cancer cells bypass the contact inhibition of proliferation programming and continue expanding by upregulating YAP/TAZ nuclear activation. The tissue of a mammary tumor is approximately 5 times stiffer and the tumor-adjacent stroma is approximately 20 times stiffer than nor-mal mammary gland tissue. In addition, the extracellular matrix (ECM) has been shown to remodel before metastasis, such that collagen and fibronectin fibrils align radially from the primary tumor and facilitate cellular migration. These ECM changes help trigger the epithelial-to-mesenchymal transition (EMT) in cancer cells. EMT occurs in healthy tissues during embryonic development, wound healing, and tissue regeneration. However, when cancerous cells at the invasive edge of the tumor undergo this transition, they display increased migration and reduced proliferation potential.

In the lungs, a cyclic shear stress is present which have been found to induce changes in the gene and protein expression of a cell, ultimately leading to altered cell behavior, including the cell's ability to remodel its microenvironment. This dynamic between chemical/biological responses elicited by mechanical stimuli has been coined as mechanotransduction. The field of mechanotransduction has gained interest for researchers studying regenerative medicine, developmental biology, and disease progression. However, many of the existing in vitro platforms for applying mechanical stimulation require cells to be seeded on synthetic substrates, which significantly alters their behavior.

SUMMARY

Systems and methods of the invention provide an actuation platform that allows mechanical stimulation of 3D cultures on a native ECM protein to more accurately model the behavior of metastasized cancer cells compared to existing, synthetic-substrate models. Actuation platforms may use magnetically (or otherwise) actuated portions to induce minute movements between a fixed portion and actuated portion therein. The fixed portion and actuated portion can be connected by a native ECM protein such as fibronectin upon which cells can be cultured. Accordingly, the actuated movement between the fixed and actuated portions can impart strain upon the ECM protein platform and cells cultured thereon. The level and frequency of that strain can be regulated to model various physiological environments.

Systems and methods of the invention may be formed on existing culture plates thereby enables high-throughput experimentation in standard culturing equipment, while utilizing a 3D physiologically-relevant environment. Furthermore, the use of standard multi-well plates allows for seamless integration into existing imaging and analysis platforms. Also, culturing on natural protein substrates (e.g., fibronectin fibrils supported by a PDMS actuator body) allows for all traditional assays such as fluorometric/colorimetric metabolic activity measurements and immunofluorescent staining and imaging, which is often a challenge in other 3D platforms Specifically here, understanding the underlying response of cells to mechanical strain can give insight into the pathogenesis of breast cancer progression, including the dormancy and latent reactivation of disseminated cancer cells. Therefore, platforms that can mimic these in-situ mechanical strains in a controlled in-vitro environment are essential to continue pursuit of knowledge in the metastatic cancer field, with far-reaching applications in adjacent fields. Multiple commercial devices exist that can mechanically induce strain on cells with varying modalities and each with their advantages and disadvantages. The ShellPA system is a pneumatic actuation platform that has precision and induces a homogenous physiologically relevant strain, 0% to 20%, deforming a synthetic substrate. This system has been used previously for pulsatile stretching. The platform, though, is impossible to implement with existing cell culture plates because of custom cell culture chambers and requires cumbersome connections for pneumatic actuation. Another cell stretching system by Strex Systems (STREX Inc.) is composed of motor driven clamps stretching a PDMS substrate to a controlled strain. These platforms have low experimental throughput, up to 8 cell culture wells, which makes testing a large number of various experimental conditions simultaneously difficult. Both of these platforms also depend on culturing the cells in a 2D non-physiological substrate limiting the similarity with the lung micro-environment as well as incurring significant costs for multiple experiments. Understanding cancer cell response in a 3D environment has become an increasingly researched topic. It has been shown that breast cancer cells specifically have significant different response when exposed to a 3D environment as opposed to a 2D substrate. Even more so when this environment is dynamic and mimicking the mechanical stimulus provided by physiological regions.

In certain embodiments, to better recapitulate the physiological conditions, systems and methods of the invention may include an actuating platform with the ability to apply tensile strain on cells at various amplitudes and frequencies in high-throughput multi-well culture plates. By suspending fibrillar fibronectin over the gaps between magnetic actuators, a more physiologically-relevant substrate for 3D cell culture which is not reliant on any underlying hydrogel can be provided.

BRIEF DESCRIPTION OF FIGURES

FIG. 5 shows actuator fabrication and characterization. FIG. 5A illustrates manufacturing of PDMS magnetic actuator with fibronectin coating. Image of actuator with fibronectin coating highlighted. FIG. 5B shows components of magnetic actuation platform FIG. 5C Deflection vs. magnetic field strength of actuator theoretical response, with or without fibronectin coating. FIG. 5D shows deflection vs. magnetic field strength of fibronectin-coated actuator depicting region of physiological strain, lower strain range (5% to 10%) and higher strain range (20% to 25%) (yellow) (n=3, Error bars designate Std. Dev.). (Scale bar=2 mm) FIG. 5E shows magnetic field strength produced by platform at actuator distance as a function of time. Transient strain experienced by fibronectin according to the model. FIG. 5F shows one cycle of fibronectin stretching at 0.3 Hz (scale bar=2 mm).

FIG. 8 shows matrix degradation under cyclic stretching.

FIG. 9 shows a model of the magnetic field in the magnet array. FIG. 9A shows placing magnets in each well of a 24-well plate (left) leads to uneven magnetic field strength which would alter the deflection response of the actuators situated above the array. FIG. 9B shows alternating the magnets (right) leads to uniform field strength and enables culturing of 12 mechanically-stimulated actuators at once.

FIG. 10 shows EdU Analysis. EdU and DAPI staining after 3 d for MDA-MB-231 cells are shown in FIG. 10A, FIG. 10C static and FIGS. 10B and 10D actuating conditions.

FIG. 12 shows fibronectin matrix degradation.

DETAILED DESCRIPTION

Figure 1A:
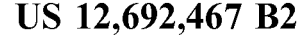
FIG. 1 shows a) Device fabrication b) Magnetic actuation platform c) PDMS actuator coated with fibronectin. d) Time lapse of fibronectin stretching with 0.3 Hz actuation Scale bar: 2 mm

Accurately replicating and analyzing the changes in cellular response to mechanical cues is vital in disease progression monitoring. However, many of the existing in vitro platforms for applying mechanical stimulation require the cells to be seeded on synthetic substrates, which is not physiologically-relevant and significantly alters cellular behavior. To better recapitulate the physiological conditions, 3D cell-culture platforms are described herein with the ability to apply tensile strain on cells at various amplitudes and frequencies using magnetic actuators in a high-throughput multi-well culture plate. By suspending a fibronectin membrane over the gaps between actuators, a physiologically-relevant substrate is provided for 3D cell culture with a high experimental throughput.

To overcome some of the challenges with traditional actuation platforms such as pneumatic and electromagnetic modalities on a non-physiological substrate, a magnetic actuation platform with high experimental throughput and the ability to seed these cells on a physiological substrate was developed. A magnetic actuating cantilever made of PDMS may be used. The device is designed so that fibronectin can attach to an area of interest in between the edge of the cantilever and the frame. The device can fit in one well of a commercial 24 well cell culture plate allowing for high experimental throughput.

In various embodiments, a first point of an ECM protein may be operably coupled to a fixed portion of the cell-culture platform and a second point of the ECM protein to an actuated portion of the cell-culture platform. The cell-culture platform may be operable to change the distance between the fixed portion and the actuated portion to impart strain on the ECM protein.

In various embodiments, the actuated portion comprises a magnet such as a permanent magnet, examples of which are discussed in the Examples below. In some embodiments, the magnet may be an electro-magnet. The actuated portion may comprise a piezoelectric material or may be operably coupled to a hydraulic or pneumatic actuator. Movements of the desired range, frequency, and force desired for various applications may be imparted through various electromechanical, magnetic, or other means.

Systems of the invention may include an actuation platform upon which the cell-culture platform may be positioned. The actuation platform may be operable to apply spatially addressable energy (e.g., magnetic fields, electrical stimulation) to individual actuated portions (e.g., wells) in order to impart strain to the suspended ECM protein and cells cultured thereon. For example, one or more electromagnets may be positioned on the actuation platform capable of generating magnetic fields of a desired magnitude configured to induce movement of the actuated portion of the cell-culture platform. The actuated portion may comprise cantilever with the ECM protein coupled to one end and a magnet coupled to the same end or an opposite end on the other side of the cantilever. Accordingly, by introducing a magnetic field to attract or repel the magnet on the cantilever, the ECM-protein-coupled end can be moved relative to the fixed portion of the cell-culture platform (e.g., a side of a well in a multi-well plate).

Strain may be imparted at various frequencies and forces depending on the desired characteristics (e.g., the physiological environment being modelled). In various embodiments, the frequency may be between about 0.001 and 100 Hz, between about 0.01 and 10 Hz, and between about 0.1 and 1.0 Hz. The strain value may be between about 0% and 100%. The strain value may be less than about 90%, about 80%, about 70%, about 60%, about 50%, about 40%, about 30%, about 20%, and about 10%.

In various embodiments, the cell-culture platform may be a multi-well plate such as a 12-well or 24-well plate where each well comprises an actuated ECM protein upon which cells can be cultured to model physiological forces.

In preferred embodiments, the ECM protein comprises fibronectin. Other ECM proteins that may be included in the suspended culture substrate may comprise collagen, elastin, laminin, and vitronectin. ECM components and proportions thereof can be selected to more-accurately reflect the native physiological environment of the cell type to be cultured.

In preferred embodiments, components of the cell-culture platform are formed of a readily available, biocompatible, inert, polymer such as polydimethylsiloxane (PDMS). Platforms may be formed using any known method depending on the material being used. For example, PDMS platforms may be machined, fabricated, or molded using, for example, a dissolvable polyvinyl alcohol (PVA) mold.

Specific embodiments have application in the modeling of physiological forces in native environments and their effects on characteristics such as cancer cell proliferation. Additional details, systems, and methods are described below in the following Examples.

EXAMPLES

Example 1

Advantages of the present device can be observed by testing multiple breast cancer cell lines, cultured on a 3D biologically-relevant substrate under cyclic strain which mimics the frequency and physiologically relevant strain of human lungs. The resulting cellular and microenvironmental transitions are presented below as a result of biomimetic forces relevant to the metastasis of breast cancer cells.

Platform design and characterization: The goal of the study is to provide an environment that imitates as close as possible the alveolar expansion and understand the cellular response. From literature, cells in the lungs experience an average strain of 14%. The actuating platform was therefore set such that the cells experienced a maximum of approximately 14% strain, with the frequency of the platform at 0.3 Hz, which corresponds to about 18 breaths per minute.

Device fabrication: To mimic the lung microenvironment a device was designed that can stretch a physiological substrate like fibronectin without having to be seeded on a 2D substrate. As depicted by FIG. 1a, 3D printed molds (Autodesk Ember, San Rafael, CA) were used to cure 10:1 PDMS formulation. The PDMS was cured in an oven for 2 hours at 100° C. After curing the PDMS, the device is removed from the molds and a 2 mm diameter and 1 mm thickness N42 NdFeB permanent magnet (KJ Magnetics, Pipersville, Pennsylvania) was placed on the reservoir and then coated with PDMS. The devices were left in the oven at 70° C. for 24 hours to ensure full curing of the PDMS.

The actuators were sterilized by soaking in 70% ethanol, rinsed three times with PBS, and left under a UV fume hood for 1-2 hours. After sterilization, to suspend the physiological substrate on the region of interest, the actuators were placed in a 100 µg/mL solution of fibronectin suspended at the air-water interface. The actuators were rotated for 2 hours on a rotisserie shaker (Barnstead Labquake, Lake Balboa, CA) and maintained at 30° C. at 8 RPM.

Figure 2:
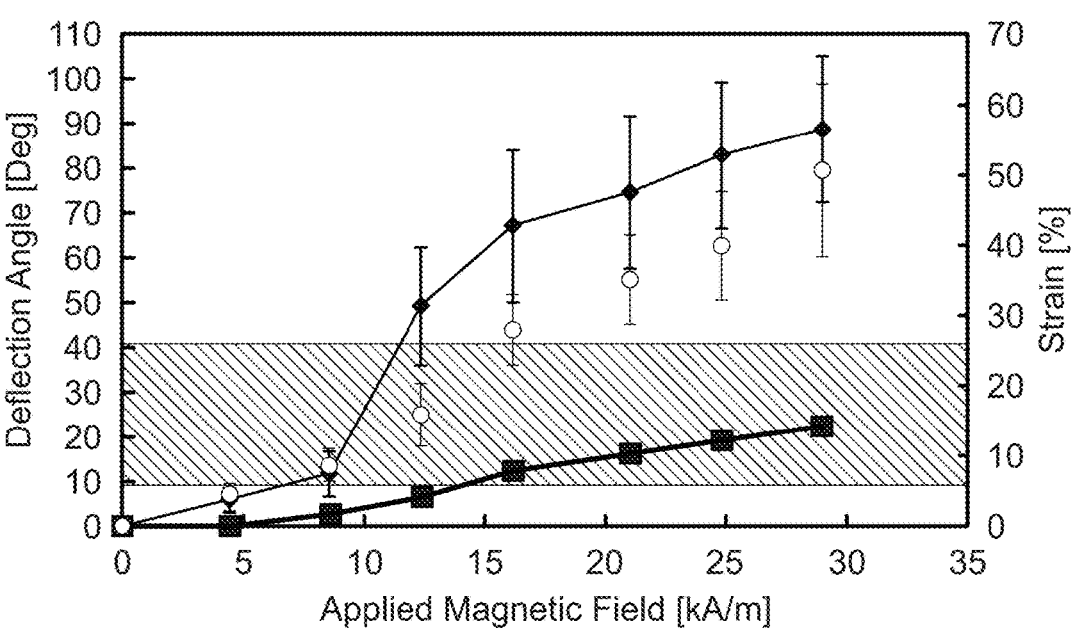
FIG. 2 shows the static response of actuators without fibronectin coating (red) and coated with fibronectin (black). Also displayed is the experimental strain of the fibronectin (gold). Gold-shaded region is the area of physio-logical relevance and interest.

Device characterization: To determine the static response of the PDMS actuator, it was placed along the long axis of a bespoke electromagnet (cylindri-cal permalloy core, 1-in-diameter and 6-in-tall with 300 turns). The actuators were posited on this electromagnet through a customized fixture to maintain the distance between the electromagnet and the permanent magnet constant at 3 mm. The electro-magnet was supplied current by a DC power supply (PWS2326, Tektronix, Beaverton, OR). The magnetic flux density supplied by the electromagnet at different currents was measured via a hall probe gaussmeter (8010, F. W. Bell, Milwaukie, OR). During actuation the device deflection angle was optically measured using a digital SLR camera (Canon 50D, Huntington, NY). This procedure was repeated for actuators with and without fibronectin coating and the results are shown in FIG. 2. The magnetic field induced varied from 0-28 kA/m for uncoated and coated actuators.

Figure 1B:
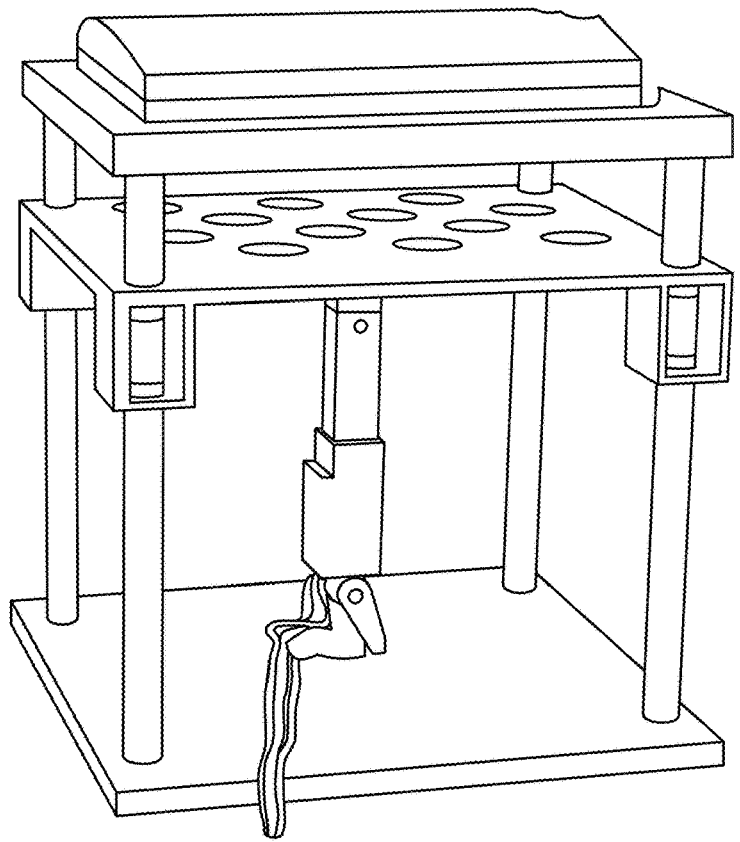
Figure 1C:
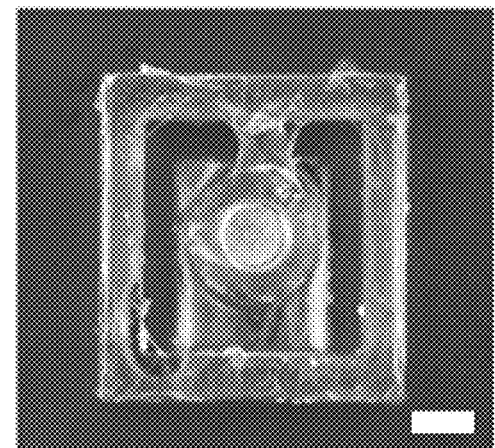
Figure 1D:

Magnetic actuation platform characterization: In order to actuate the magnetic PDMS devices and to overcome some of the challenges presented by other cell stretching systems, a platform was developed to easily integrate a 24-well culture plate for 3D cell study. The platform as shown in FIG. 1*b* contains a linear actuator (Actuonix, Alberta, BC, Canada) programmed to move an array of permanent magnets of 19 mm in diameter and 2.4 mm thick towards a fixture suspending the multi-well culture plate. Each of the actuators is anchored by a PLA 3D printed fixture to avoid reorientation of the actuators when exposed to the force due to the translation of the magnets.

Figure 3:
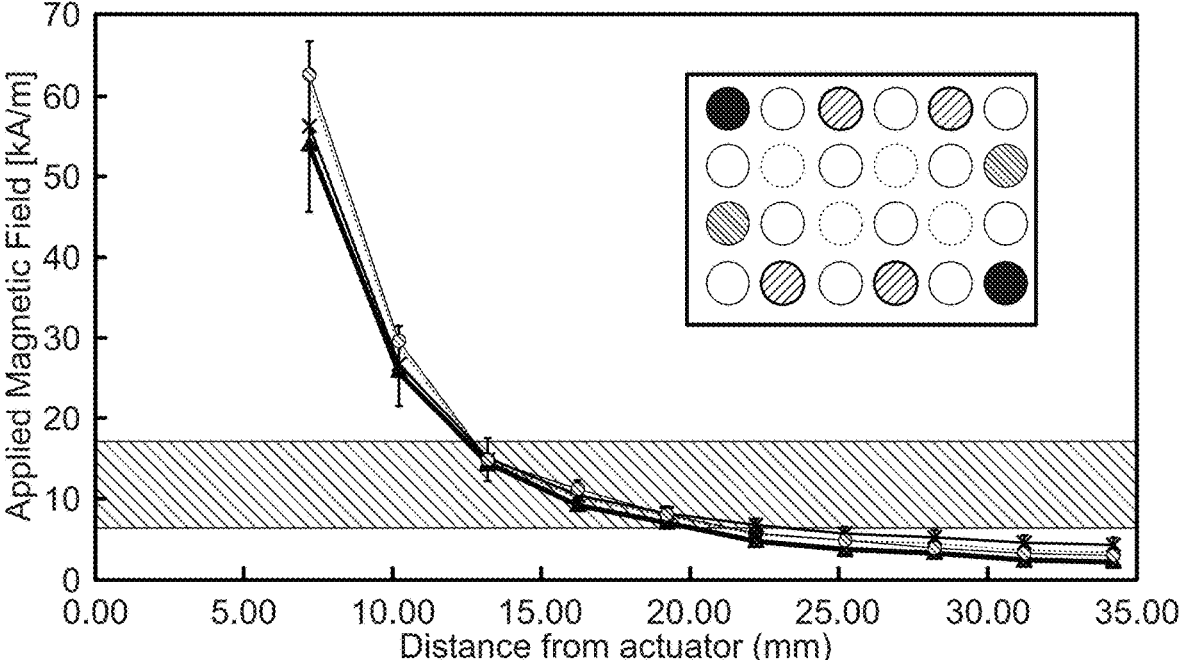
FIG. 3 shows magnetic actuation platform characterization showing the magnetic field strength as function of the distance from the actuator. The shaded region is the area of physiological relevance and interest

The magnetic field distribution of the permanent magnet array was determined experimentally via a hall effect gaussmeter described earlier in the section of the characterization of the de-vices. Each of the magnets on the platform was measured at 3 mm z-axis increment distances starting from the maximum travel of the linear actuator representing the closest the platform could reach the actuators. FIG. 3 shows the distribution of the magnetic field with each color representing a different configuration of magnets in the platform.

Viability Studies: 72,400 cells were seeded at high density (in 40-100 uL of media) onto the suspended fibronectin on the actuators in non-adherent 24 well plates. Media used was DMEM/high glucose with 10% FBS and 1% antibiotics. The E2 parental line additionally had 1% insulin. After 2 hours, additional media was added to cover the devices (800-1000 uL). After an additional 7 hours, devices that would experience mechanical stress were moved to new wells and placed on the platform to begin cyclic actuation. This allowed the cells time to adhere to the fibronectin such that the mechanical force did not remove them from the devices. Actuating devices remained on the platform for 7 days. Control devices remained static for the same duration. A resazurin colorimetric assay (Sigma TOX8-1KT) was performed on days 1, 2, 4, and 7. Briefly, media was removed and 1 mL of 10% resazurin solution (diluted in phenol-red free completed media as described above) was added to each well. After 2 hours, 3 samples from each well were read using fluorescence (excitation 560 nm, emission 590 nm). The remaining resurazin solution was removed completely and replaced with completed DMEM/high glucose.

YAP/TAZ Assay: 18,100 cells were seeded at high density onto the suspended fibronectin on the actuators in non-adherent 24 well plates. After 1 hour, 1000 μL of media was added to cover each well and the mechanical-stimuli group was moved to the actuating platform to begin actuation. After 24 hours in culture (23 hours actuating for the corresponding group), actuators were fixed with 4% paraformaldehyde at 4 C, and then washed and stored in PBS. Actuators were stained against DAPI, actin-AF488, YAP, and fibronectin. Anti-FN in rabbit (Sigma 3648), 1:200 dilution. Anti-YAP in mouse (Santa Cruz H-9), 1:200 dilution. Phalloidin conjugated to AlexaFluor 488), 1:40 dilution. DAPI, 1:500 dilution. Imaged on a Zeiss inverted confocal.

Drug Sensitivity Analysis: Seeding density, when to start actuating, what concentration of drug to give, how cell death was determined, IC50 values.

RNA Sequencing: Seeding density, when to start actuating, how RNA was isolated.

Determining the reorientation/inhibition of extracellular matrix: The platform enables the study of ECM manipulation when cells are exposed to an environment of cyclical strain. An experiment was designed to study varying degrees of metastatic breast cancer cell lines such as non-metastatic (E2 parentals), moderately metastatic (CA1A), aggressively metastatic (MDA-MB-231) and finally as a control group the HLF. Each cell line, as well as a control no-cell, was separated into two groups static, was not placed in the platform and did not receive any magnetic fields and actuating, on the platform receiving cyclical mechanical strain, for one week.

Figure 4:
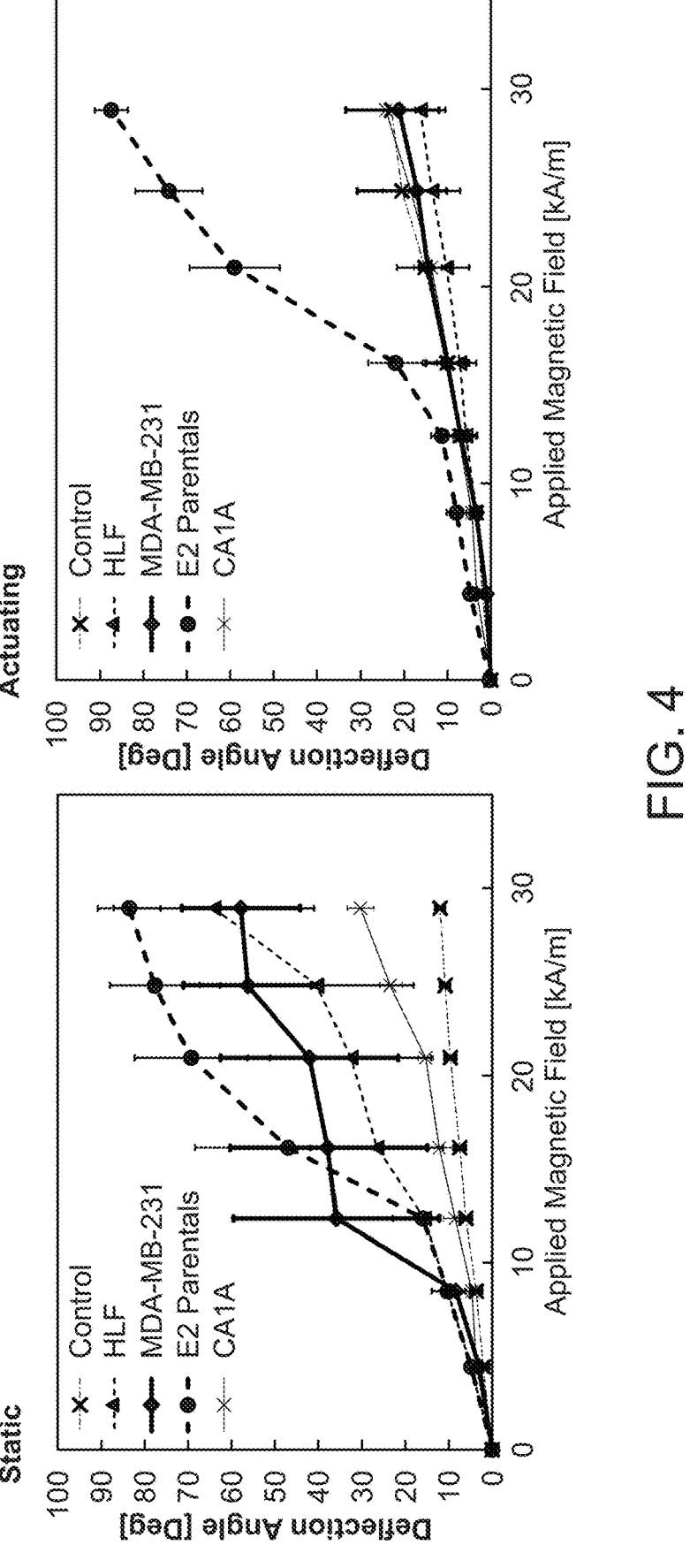
FIG. 4 shows deflection response of control (no cell), human lung fibroblast cells, and 3 different breast cancer cell lines after one week of actuation (black) and one week of being static (red).

FIG. 4 demonstrates the deflection response of the actuators after one week of being seeded with cells. By comparing the static and actuating groups' deflection response it is evident that all the static group cell lines experience matrix reorientation or degradation that allows it to become more susceptible to FN matrix fracture. This result is further supported by seeing that the control group with no cells seeded has a stiffer FN matrix.

It has previously been demonstrated that human lung fibroblasts exposed to a cyclic strain environment reorient their matrix as a response and when co-cultured with cancer cells they can alter their migration. After one week of in-vivo like actuation in an in-vitro environment, three of the four cancer cell lines and the human lung fibroblast have a stiffer response to the magnetic field. For Human Lung fibroblast it is known that they are able to reorient ECM but for the breast cancer cell lines it is believed that in a cyclical strain environment they undergo dormancy and therefore are unable to break down the matrix.

Example 2

Introduction

Over the past two decades, there has been a significant increase in elucidating the effect of mechanical tissue changes on solid cancer progression. Mechanical forces are being recognized as an integral part of the tumor microenvironment and are heavily intertwined with research on cancer associated fibroblasts, tumor invasion, and chemotherapeutic delivery. In breast cancer, the tumor and the surrounding stroma are approximately 5-20 times stiffer than healthy mammary gland tissue. In the primary tumor environment, this stiffening may enable Yes-Associated Protein/Transcriptional activator with PDZ binding motif (YAP/TAZ) nuclear activation, which, among other things, enables cells to bypass the contact inhibition of proliferation and continue dividing. The extracellular matrix (ECM) stiffens through increased protein deposition, primarily via collagen I and fibronectin accumulation, as well as increased cross-linking via lysyl oxidase (LOX) secretion. As tumors grow, solid stress and interstitial fluid pressure also increase. These compressive forces can alter gene expression and cell function in the tumor and tumor-associated cells. They also deform blood and lymphatic vessels, which reduces the delivery of oxygen and nutrients, creating the well-known hypoxic and acidic microenvironments at the center of the tumor. These compressed vessels inhibit the delivery of chemotherapeutic drugs, compromising therapeutic outcomes. There is ample evidence of matrix remodeling during primary tumor progression and invasion. For example, as collagen and fibronectin fibrils accumulate, they initially orient parallel to the tumor borders. In invasive tumors, fibril bundles reorganize and orient perpendicular to the tumor, acting as 'tracks' for enhanced tumor cell migration through the basement membrane and into the vascular system. Lastly, there is extensive exploration of the mechanical forces related to disseminated tumor cell survival in the vasculature. Circulating tumor cells are thought to survive the shear stress by several mechanisms, including reorganizing their cytoskeleton, altering cytokine expression to avoid anoikis, and donning a protective layer of thrombi.

A currently under-explored area of mechanotransduction in cancer is the effect of dynamic aberrant forces on disseminated tumor cells in distant organs. The two most common sites of metastasis in breast cancer are the bones and the lungs, which natively undergo cyclic compressive and tensile stresses, respectively. Nevertheless, the effects of these native mechanical stimulation on the phenotypic and genetic changes of disseminated tumor cells are not yet known.

Current platforms for applying cyclic tensile forces do so primarily on 2D synthetic substrates. Yadav et al. developed a platform to apply cyclic tensile stimulus with 1.4% strain at 0.1 Hz for up to 4 h to different breast cancer cells cultured directly on a synthetic substrate. See S. Yadav, R. Vadivelu, M. Ahmed, M. Barton, N. T. Nguyen, Stretching cells—An approach for early cancer diagnosis, Exp Cell Res 378(2) (2019) 191-197; S. Yadav, M. Barton, N.-T. Nguyen, Stretching Induces Overexpression of RhoA and Rac1 GTPases in Breast Cancer Cells, Advanced Biosystems 4(2) (2020) 1900222; the content of each of which is incorporated herein by refrence. They reported significantly higher expression levels of RhoA and Rac1 in stretched breast cancer cells, as well as cell death in the prolonged stretching. Commercially, three companies currently exist which provide platforms to mechanically stretch cells. These are the STREX Cell Stretching System devices (Strex Inc., Osaka, Japan), the ShellPA platform (Menicon Life Science, Aichi, Japan), and the Flexcell International Corporation with a line of devices under the Cell Stretching Bioreactor Systems name (Flexcell International, Burlington, North Carolina). Overall, although there are multiple applications of these devices, they are severely limited—often by requiring specialized culturing plates, or having bulky pneumatic connections resulting in cumbersome cell culture. Most importantly, these devices force the culturing of cells in 2D, which drastically alters cell behavior. Although STREX and Flexcell have newer products which enable compression of collagen gels, embedding cells in a hydrogel of varied stiffness complicates the study of cyclic loading and does not enable tensile stretching without possible fissures in the gel.

In this work, a simple actuation platform was developed that can enable mechanical stimulation of 3D cultures on a native ECM protein to better recapitulate the behavior of metastasized cancer cells. A magnetic actuation platform was engineered with 3D fibronectin culturing substrate to study the effect of cyclic tensile force on breast cancer cells. This actuation system mimics the native lung microenvironment without the confounding effects of synthetic 2D culturing or encapsulating hydrogels. This platform is compatible with standard 24-well plate culture dishes, creating a high-throughput design. This simple new platform can be used to capture the effects of biomimetic cyclic strain on cancer cells and their surrounding microenvironments. Cyclical tensile strain of the suspended breast cancer cells displayed a reduced rate of proliferation and preserved fibronectin integrity when compared to the static counterparts. Importantly, the tensile loading did not cause cell death, even after week-long culturing. These findings indicate mechanical force in the lungs as a potential suppressor of metastatic outgrowth in breast cancer, potentially linked to the dormancy and latent reactivation of breast cancer metastases, and clearly demonstrate the need for robust, physiologically-relevant studies which incorporate mechanical forces.

Results

Applying 3D Physiologically-Relevant Strain to Fibronectin with Magnetic Actuators To mimic the lung microenvironment, a soft actuator capable of inducing a range of strain experienced in the alveoli was designed. The actuator is comprised of three main components (FIG. 5A). The body includes an outer frame and a central cantilever. The body is made out of polydimethylsiloxane (PDMS) for structural integrity. A permanent magnet is embedded in the end of the cantilever. Fibronectin fibrils are suspended across the gap between the cantilever and the body frame (FIG. 5A). The suspended fibronectin fibrils enable a 3D culturing region of interest that is not affected by stiff scaffolding or a hydrogel. Each actuator fits within the 16 mm diameter well of a standard 24-well culture dish. When an external magnetic field is applied, the cantilever deflects out of plane. By varying the magnitude of externally applied magnetic fields, $H_{ext}$, the amount of out-of-plane deflection, $\phi$, given by:

$$\phi = \frac{V_{mag} M \times H_{ext}}{k_{beam}}$$

can be controlled. With volume of the permanent magnet $V_{mag}$, magnetization M, and beam angular stiffness $k_{beam}$.

To automate cyclic mechanical stimulation, the custom-made permanent magnet array was fitted with a linear actuator that can be controlled using a microcontroller (FIG. 5B). This enabled us to easily change the working distance as well as the speed and the frequency of actuation. Based on the following numerical model to predict the magnetic field applied on the magnetic actuator as a function of distance, $$B = \frac{B_r}{2}\left(\frac{D+z}{\sqrt{R^2 + (D+z)^2}} - \frac{z}{\sqrt{R^2 + z^2}}\right),$$

and the experimental results (FIG. 9), it was determined that the magnet array should move between 13.2 and 19.2 mm from the actuators to achieve the desired magnetic field strength range (FIG. 5C, FIG. 5D) B, $B_r$, D, z, and R are the magnetic field experienced at a distance z from the magnet, the magnetic remanence of the permanent magnet, the thickness of the magnet, the distance from the surface of the magnet, and the radius of the magnet respectively.

Figures 9C, 9D:
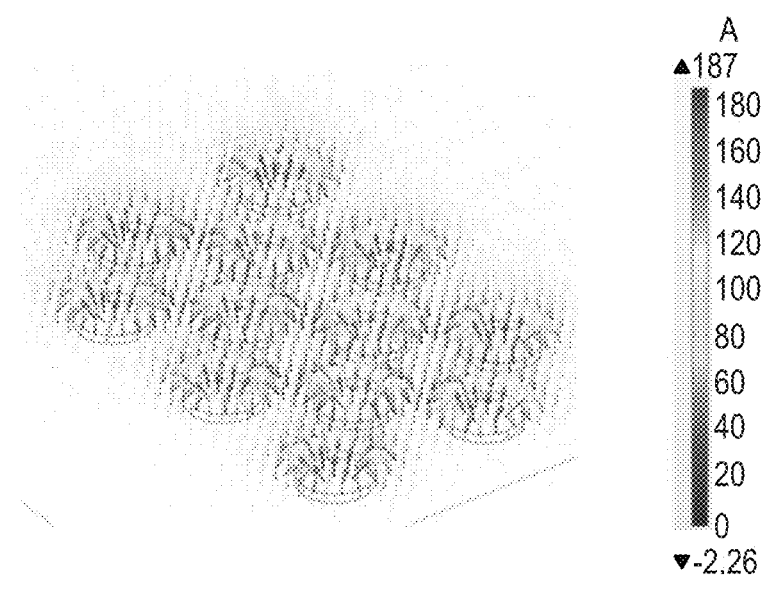
FIG. 9C shows magnetic vector field of alternating array of permanent magnets.
FIG. 9D shows applied magnetic field of permanent magnet array vs. the distance from the actuator. Gold bars depict desired range of applied magnetic field necessary as a function of array distance to actuator. (n=12, Std. Dev.).

The moving platform was constructed with permanent magnets underneath alternating wells. It was determined that this permanent magnet arrangement resulted in the most uniform magnetic field across 12 of the 24 well culture plate through computer simulation (FIG. 9). Lastly, the magnetic platform was programed to apply the cyclic mechanical stretching to the actuators at a frequency of 0.3 Hz (FIG. 5E and FIG. 5F), which mimics the average respiration rate (18 breaths per minute) for adults. With the majority of women being first diagnosed with breast cancer between approximately 60-85 years old in the United States, 0.3 Hz was deemed physiologically appropriate. Overall, the actuator and moving permanent magnet array platform enable a 3D cell culture platform with highly-customizable mechanical stimulation in high-throughput and expandable manner.

Using this system, first the amount of strain the actuators can apply on a suspended fibronectin mesh was determined.

By measuring the change in deflection angle, it was possible to calculate the amount of strain applied on the fibronectin mesh (FIG. 5C, Methods). As expected, the actuators coated with fibronectin mesh showed significant reduction in static deflection angle due to added stiffness (FIG. 5C and FIG. 5D). From this, a desired deflection angle between 2-12° was calculated to achieve physiologically-relevant strain value of 5-25%. Subsequent cell studies were then performed at a low strain rate (5-10%) or a high strain rate (20-25%), marked on the graph as LS and HS, respectively (FIG. 5D).

Metabolic Activity of Cells Reduces Due to Tensile Stress

The effect of cyclic mechanical stretching was tested on three breast cancer cell lines and human lung fibroblasts (HLF). The breast cancer cell lines are MDA-MB-231 (231), HME2, and MCF10CA1a (Ca1a). MDA-MB-231 is a triple negative, highly invasive, metastatic human cell line that was isolated from a pleural effusion in the lung. The human mammary epithelial cell line (HMLE) was HER2 transformed to produce the HME2 cells. They are capable of primary tumor formation, but have no invasive or metastatic potential. Lastly, the Ca1a cells are an epithelial-sorted breast cancer cell population derived from H-RAS-transformed MCF-10AT cells. They are triple negative as well and have slight metastatic potential, but retain their epithelial state in vitro rather than the MDA-MB-231 mesenchymal-like state (Table 1).

TABLE 1

Relative comparison of breast cancer lines used.

|  | MDA-MB-231 | HME2 | Ca1a |
|---|---|---|---|
| Hormone Status | Triple-Negative | HER2+ | Triple-Negative |
| Phenotype | Mesenchymal-like | Epithelial-like | Epithelial-like |
| Migratory/ Invasive | Very (+++) | Little (+) | Little (+) |
| Metastatic Potential | Some (++) | None (−) | Little (+) |

Figures 6A, 6B, 6C, 6D:
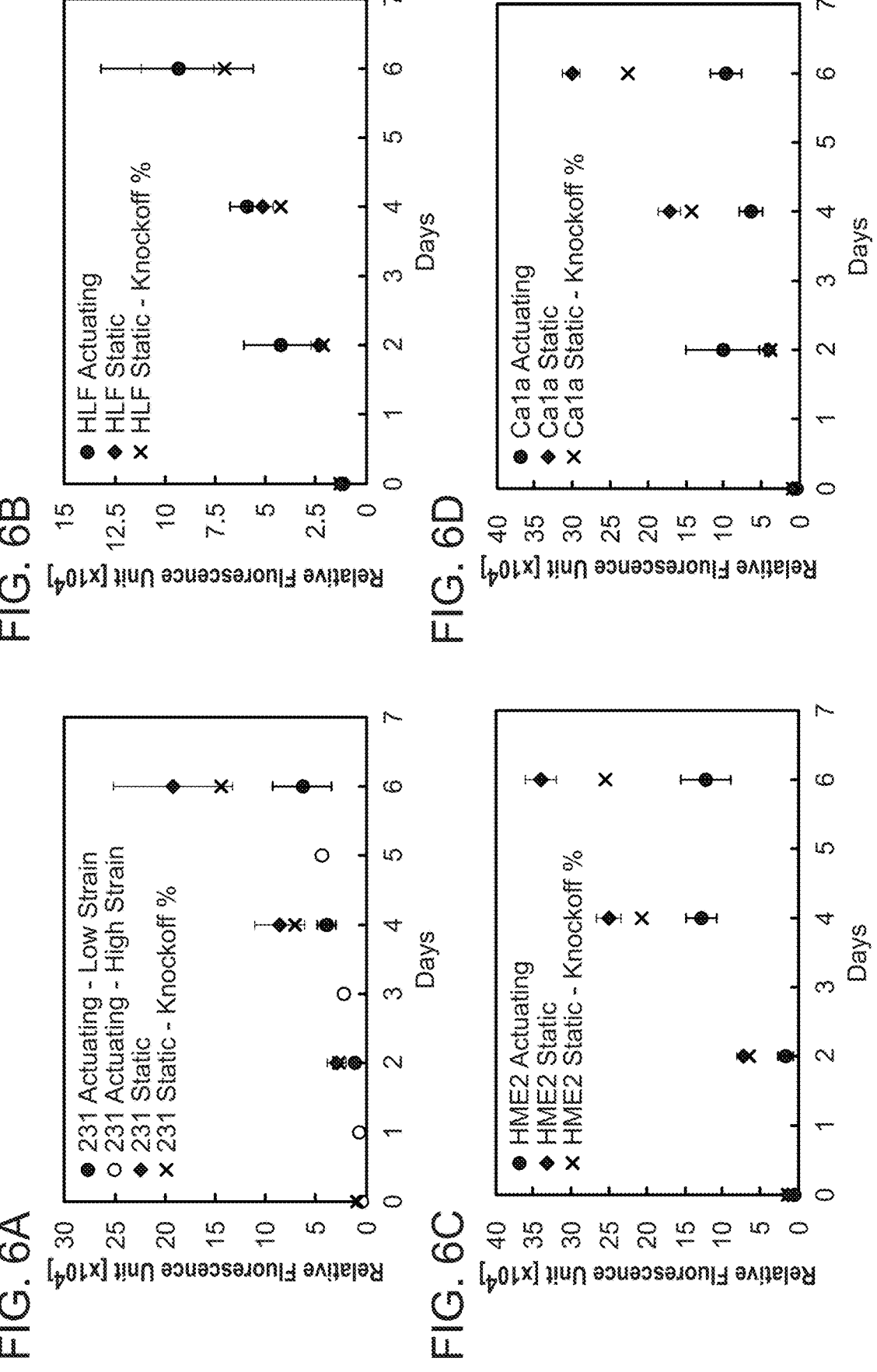
FIG. 6 shows that actuating reduces proliferation. Metabolic activity is analyzed for cells in static conditions or under cyclic actuation in FIG. 6A MDA-MB-231 cells, FIG. 6B human lung fibroblasts, FIG. 6C HME2 cells, and FIG. 6D Cala cells. The knockoff percentage is subtracted from the static values as a daily compounding rate (illustrated with an x).
FIG. 6E shows normalized growth rates from the metabolic data indicate significant growth reduction in 231, Cala, and HME2 cells, with no difference seen between the low and high strain actuation in 231 cells.
FIG. 6F shows staining of MDA-MB-231 cells after 6 d under high strain conditions shows live and dead cells with the quantified viability. scale bar is 100 μm. (*=p<0.05) (n.s.=p>0.5)
Figure 6F:
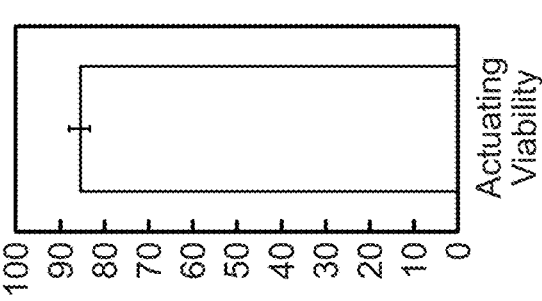
Figure 6F:
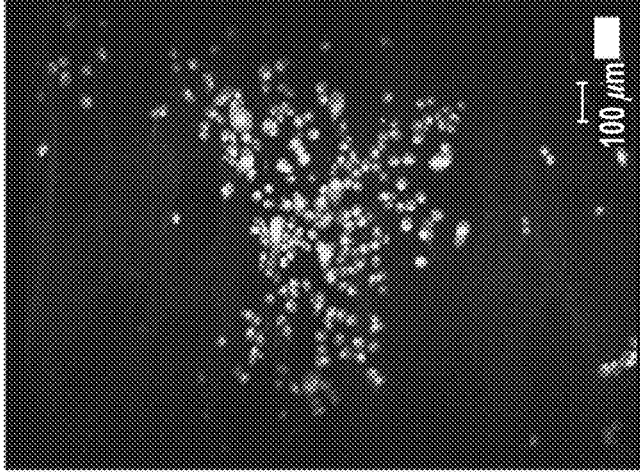
Figure 6E:
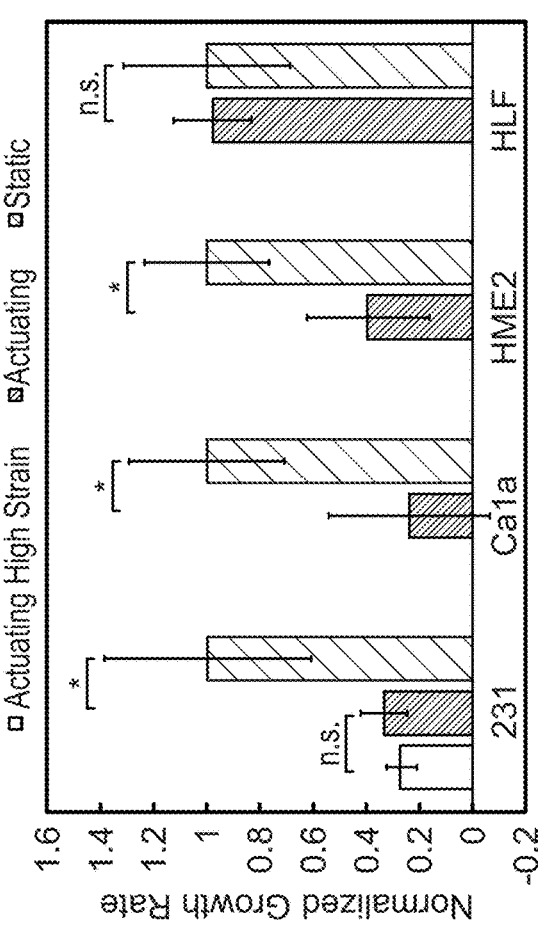

Cells were seeded in a low media volume onto the fibronectin region of interest and covered with additional media after 1-2 h. This resulted in an average seeding efficiency of 31.85% which is typical for a suspended porous structure. By counting the cells in the supernatant after 24 h of actuation, it was determined that actuation does not dislodge cells. A maximum daily knock-off percentage of 4.68% was calculated. This is an overestimate, as it assumes no cells in the supernatant in static cultures and that all floating cells in actuating groups are due to mechanical dislodging, which attributes no rate of typical cell death. In all three breast cancer lines, cyclic actuation significantly reduced the global metabolic activity of the sample, detected via resazurin (FIGS. 6A, 6C, 6D, and 6E). This was replicated for 231 cells undergoing the high strain regime. No statistical difference was seen in the growth rate between low and high strain, indicating that, at a global level, 5-10% strain is already sufficient to inhibit the majority of cell proliferation (FIGS. 6A and 6E). Importantly, all static samples were still cultured on the fibronectin-coated actuators, but they were not placed on the moving magnetic array platform. This removed bias between the groups, including those that may have resulted from a cell's different 3D and 2D proliferation rates, seeding efficiencies, and biological stimulus of the fibronectin. The mechanically-induced reduction in metabolic activity is not seen in human lung fibroblasts, indicating that the tensile force is only detrimental to a non-native cell (FIGS. 6B and 6E). The knock-off percentage was subtracted from the static cultures values as a daily compounded rate to further demonstrate that this reduction in metabolic activity is not solely a function of the mechanical force dislodging the breast cancer cells (FIGS. 6A-6D).

Figure 10F:
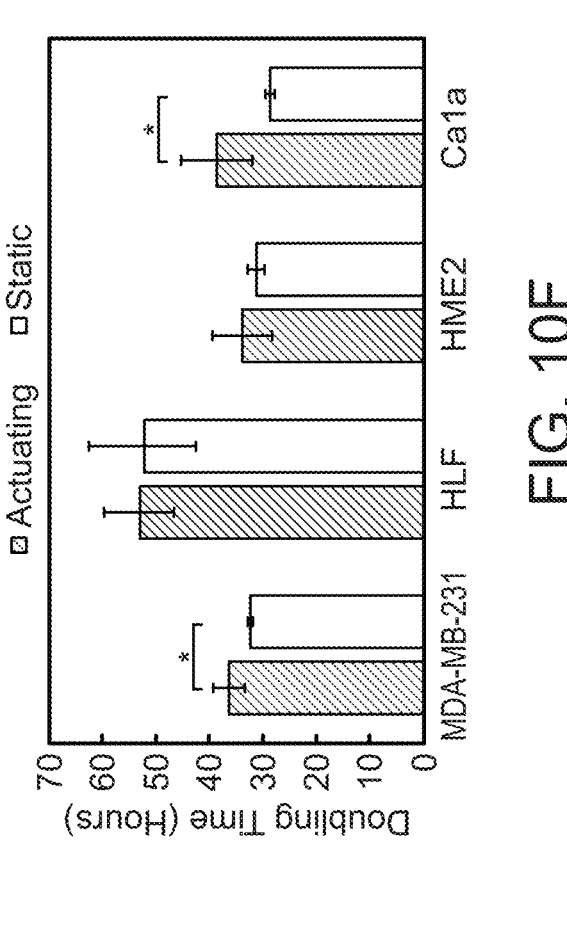
FIG. 10F shows doubling time of the actuating and static cells. (*=p<0.5).
Figure 10E:
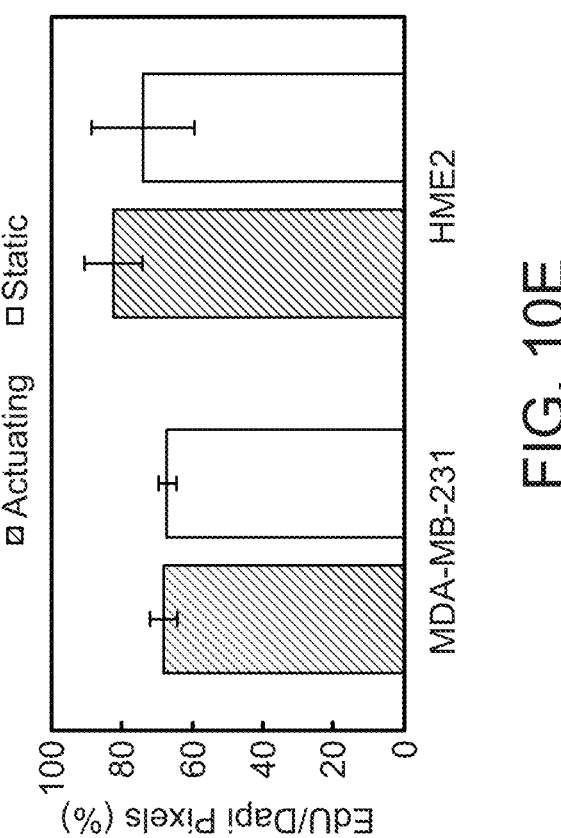
FIG. 10E shows calculated percentage of EdU positive cells.

Immunofluorescent images of the MDA-MB-231 cells after 3 d in culture show significantly more cells on the static devices (FIG. 10). Live/Dead staining of a sample after 6 d of high-strain actuation shows that the mechanical force was not inducing widespread apoptosis (FIG. 6F). The calculated doubling time significantly increased in 231 and Ca1a cells due to cyclic stretching (32 to 36 h and 28 to 38 h, respectively). Despite this, no statistical difference was seen in the percentage of EdU positive cells after 3 d of culturing for MDA-MB-231 or HME2 cells, with both static and actuating conditions entering S phase within 11 h (FIG. 10).

Cyclic Stretching Alters Cellular Morphology and Mechanotransduction

Figures 7A, 7B:
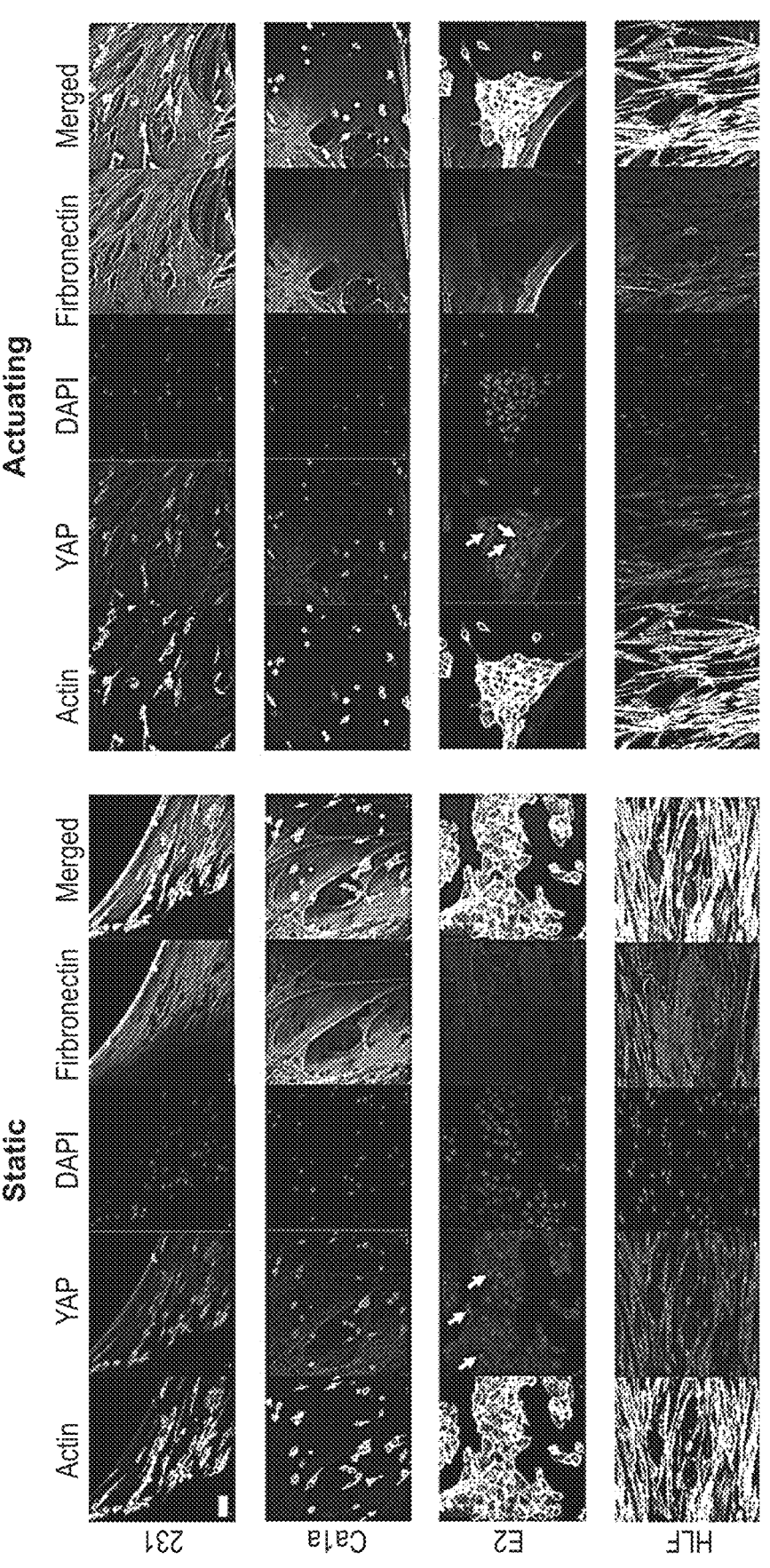
FIG. 7 shows a morphological and mechanotransduction assessment. Immunofluorescence of cells after 24 h is shown in (FIG. 7A) static or (FIG. 7B]) actuating conditions. Scale bar is 60 μm.
FIG. 7C shows the ratio of YAP in the nucleus or cytoplasm, averaged for every cell imaged per condition.
FIG. 7D shows the weighted average cluster size in each condition.
FIG. 7E shows the circularity of cells which were not in clusters per condition. 1 denotes a perfect circle. (*=p<0.05).
Figure 7C:
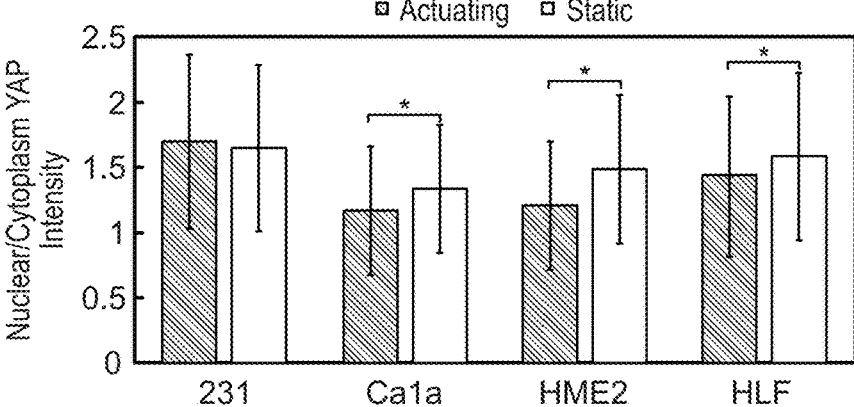
Figure 7D:
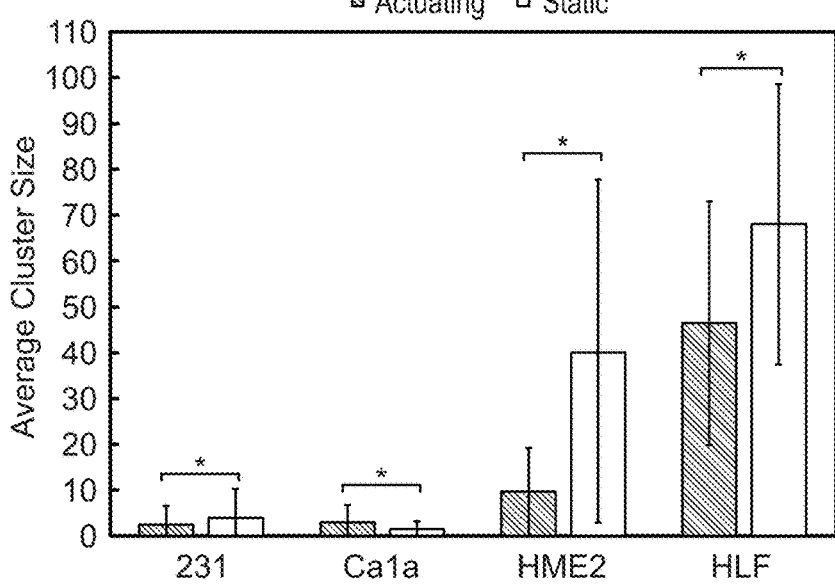
Figure 7E:
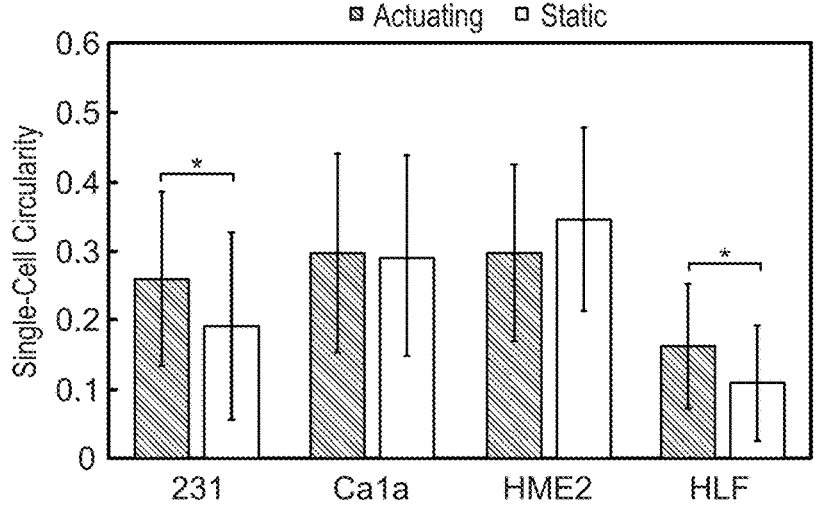
Figures 11A, 11B:
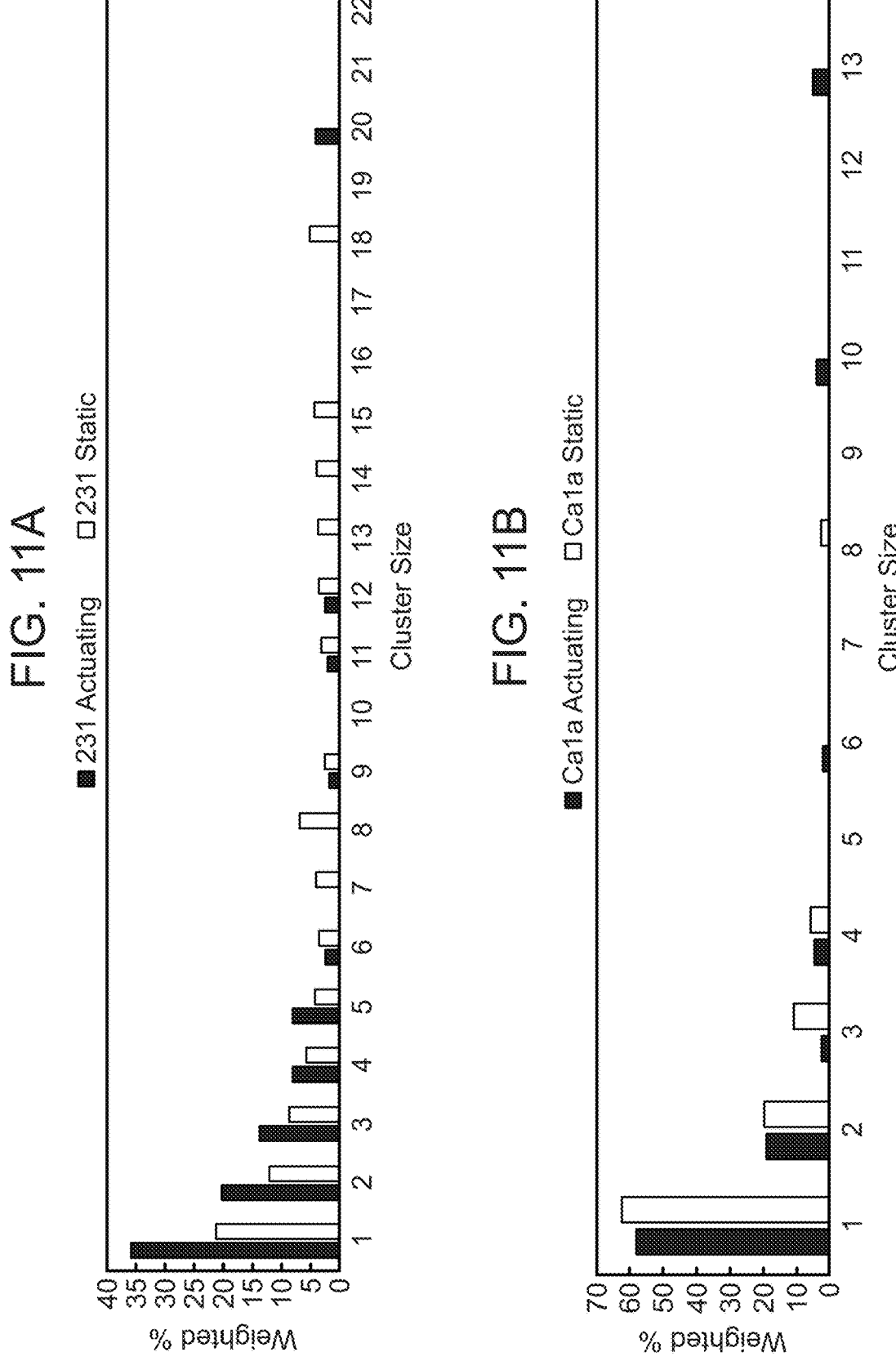
FIG. 11 shows distribution of cluster sizes. The weighted percentage distribution cluster sizes in actuating and static cultures of the FIG. 11A MDA-MB-231, FIG. 11B Cala, FIG. 11C HME2, and FIG. 11D HLF cells.
Figures 11C, 11D:
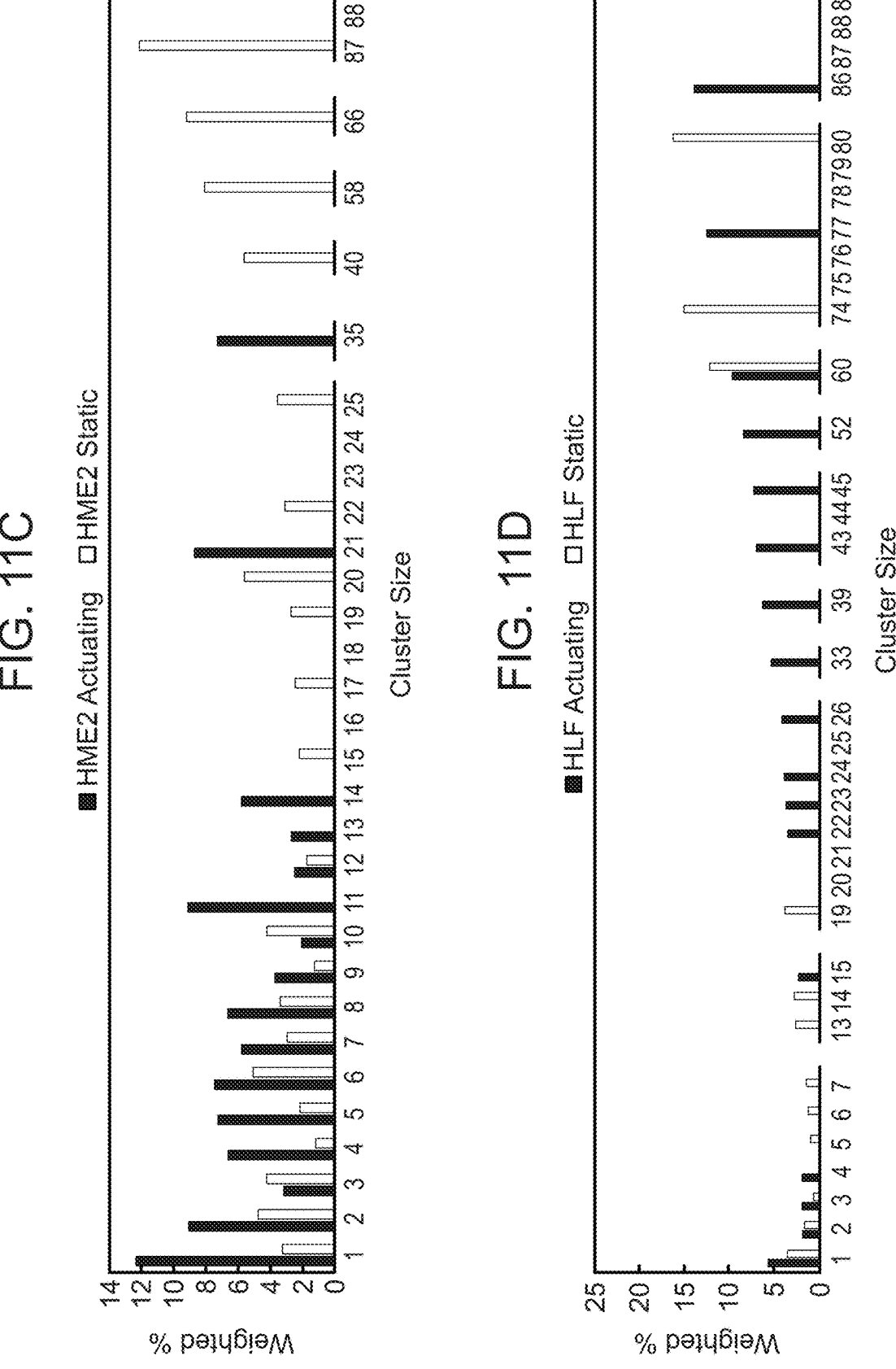

The Yes-Associated Protein (YAP) and its paralog, TAZ (transcriptional co-activator with PDZ-binding motif) are well-known regulators of the Hippo pathway and relay mechanical information into biochemical response in a process known as mechanotransduction. In healthy cells, mechanical strain, including cyclic strain, has been reported to induce YAP/TAZ activity. YAP colocalization to the nucleus or cytoplasm after 24 h in culture was analyzed, where a larger ratio of YAP in the nucleus indicates more YAP activation in the cell. Interestingly, a higher YAP co-localization into the nucleus was found, indicating that the transcriptional factor is active, in static cultures for all cell types except the MDA-MB-231 line. The MDA-MB-231 cells show no difference in YAP activation between cultures (FIGS. 7A-C). The morphology of the cells was then investigated by analyzing the weighted average cluster size and the circularity of single cells. All cell lines had a significant difference in cluster size due to cyclic strain. The MDA-MB-231, HME2, and HLF cells had smaller cell clusters on average in actuating conditions, while Ca1a cells had a higher average cluster size under mechanical strain (FIG. 7D). On average, the HLF and HME2 cells also had significantly larger cell clusters than the other two cell lines, although the HLF cells may be in more close contact due to their significantly larger cell bodies. Actuation decreased the maximum cluster size seen from 14 to 8 cells in Ca1a samples and increased the maximum cluster size seen from 20 to 23 in MDA-MB-231 samples, 30 to 90 cells in HME2 samples, and 86 to 96 cells in HLF samples (FIG. 11). Single cells were segmented and their circularity was measured such that a zero indicates no circularity and a one is perfectly circular. Only the morphology of the mesenchymal cells was significantly affected by the mechanical stimulation. MDA-MB-231 and HLF cells both became more circular in actuating conditions (FIG. 7E).

Cells in Cyclic Mechanical Stimulus Alter Suspended Fibronectin

Figures 12A, 12B:
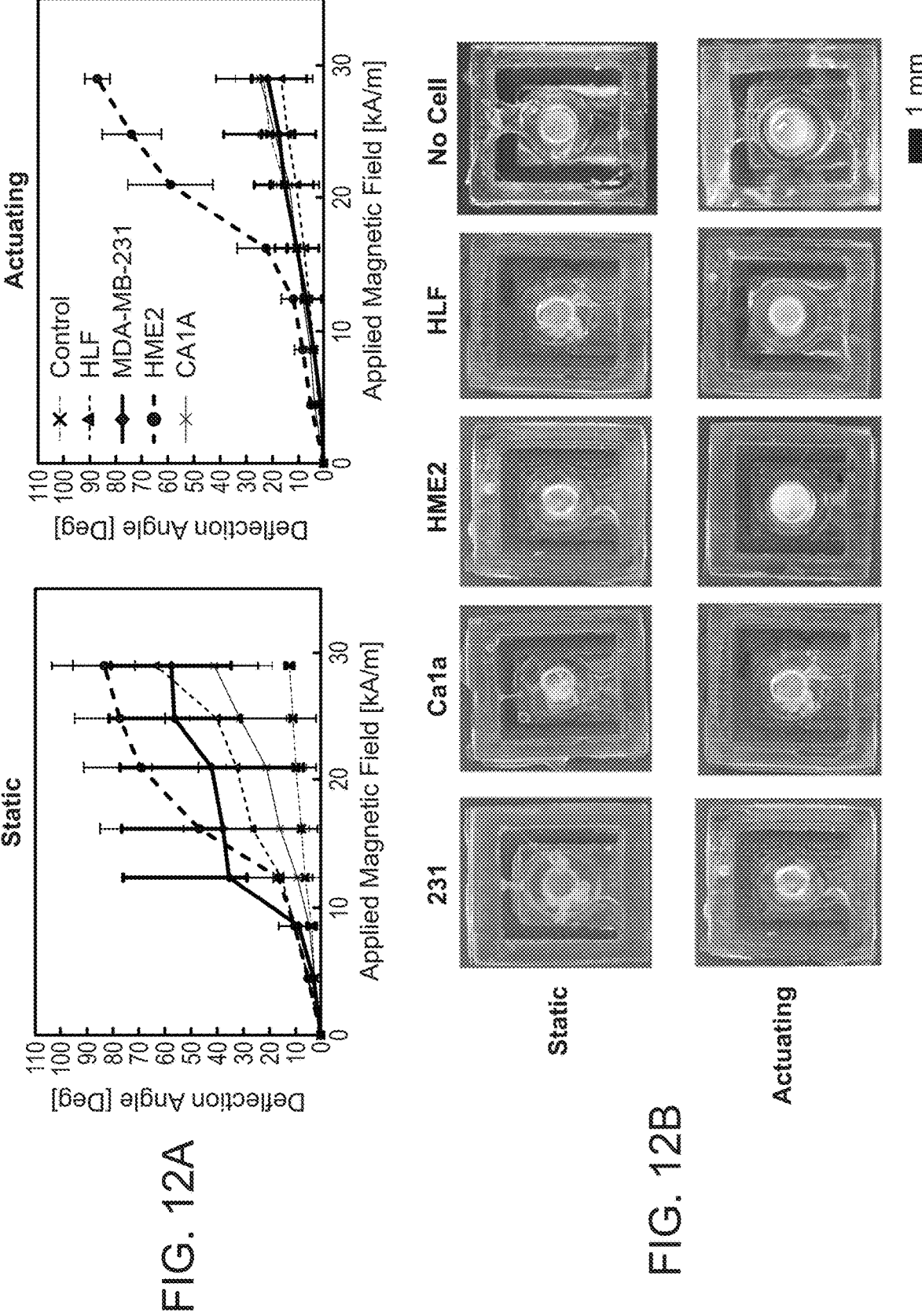
FIG. 12A shows deflect angle graphs plotted against mechanical stimulation for static or high-strain groups allow direct comparison against no-cell controls.
FIG. 12B shows images of the actuators demonstrates that cyclic stretching at 5-10% strain did not inhibit matrix breakdown. Very slight fibronectin can be seen on some static actuators. However, it immediately breaks if the actuators are placed on the magnetic array platform, such that there is no difference seen in deflection angle between actuating and static groups.

Breast cancer cells are known to modulate fibronectin levels in the ECM during disease progression. As a primary tumor or metastatic lesion develops, fibronectin and other ECM proteins, like collagen I, accumulate and result in a stiffer matrix. However, breast cancer cells have also been known to influence breakdown of the ECM, often through releasing matrix metallopeptidases, in order to enhance invasion toward the bloodstream. When metastases are first diagnosed in breast cancer, they are on average softer than the surrounding normal tissue, which is believed to prevent dormancy of the disseminated cells and facilitate the transition back to an epithelial phenotype. To assess the integrity of the suspended fibronectin fibrils, deflection tests were performed on actuators after being cultured in static or stretching conditions for one week. Directly from culture, the deflection angle of the cantilever was measured in response to increasing magnetic field strengths. As demonstrated previously, a larger amount of in-tact fibronectin will result in a smaller deflection angle at the same magnetic field strength (FIGS. 5C and 5D). In actuators without cells, the cyclic strain over the week did not disrupt the strength of the fibronectin. In static cultures, actuators from all four cell lines had higher deflection angles than control actuators, suggesting a breakdown of the matrix by the cells (FIG. 12). This breakdown also caused the fibronectin region of interest to completely tear in some of the actuators during the deflection test (FIG. 8B).

Figure 8A:
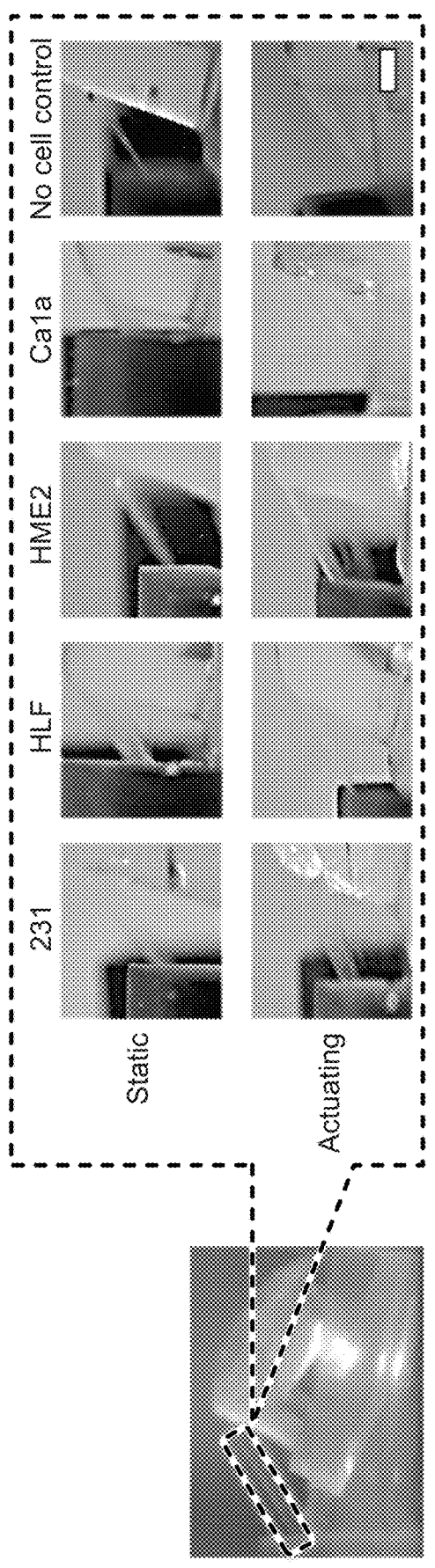
FIG. 8A shows pictures highlighting fibronectin between actuator cantilever and edge.
Figure 8B:
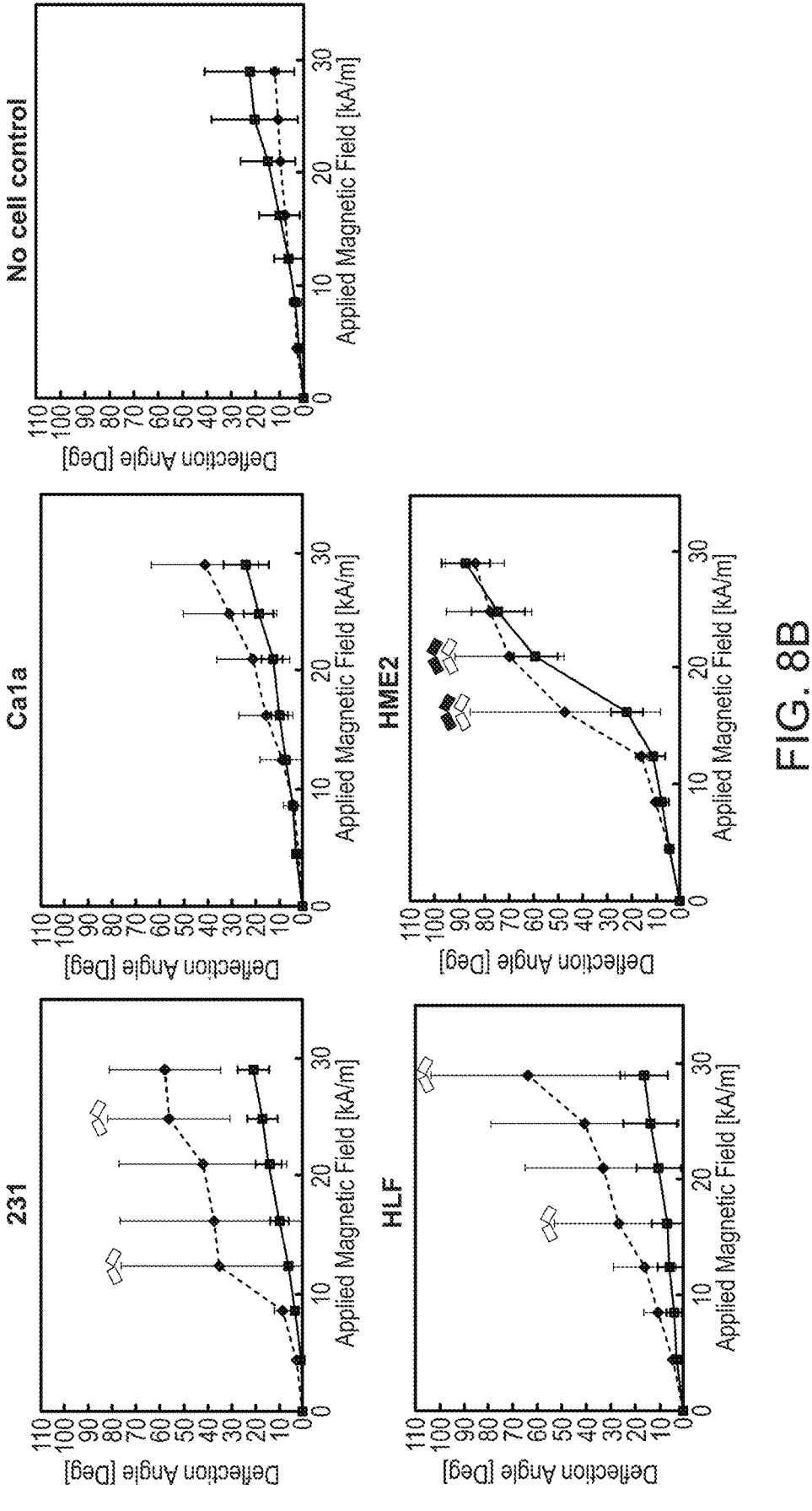
FIG. 8B shows deflection vs applied magnetic field of MDA-MB-231, Cala, HLF, and HME2 cells as well as no-cell controls. Static and actuating results are depicted for one week. Fibronectin rupture is pictorially indicated. (Error bars are Std. Dev, n=3)
Figure 8D:
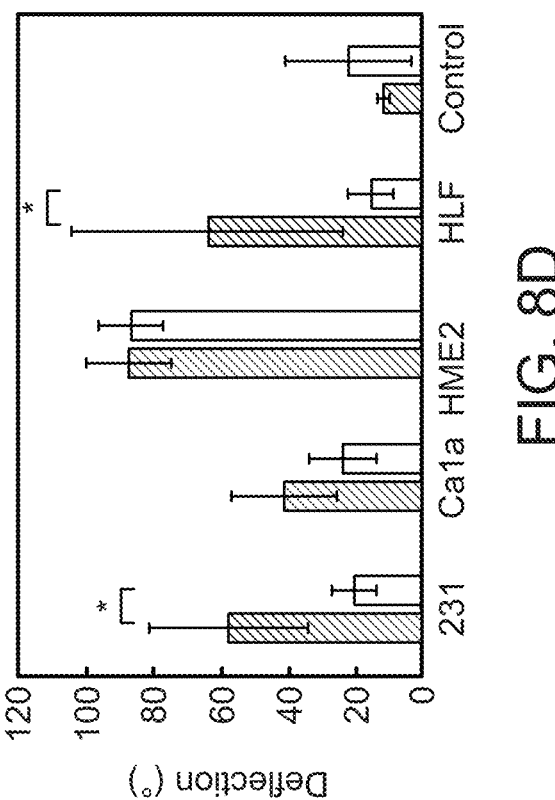
FIG. 8D shows deflection angle at maximum applied magnetic field in measurement setup (29 kA/m).
Figure 8C:
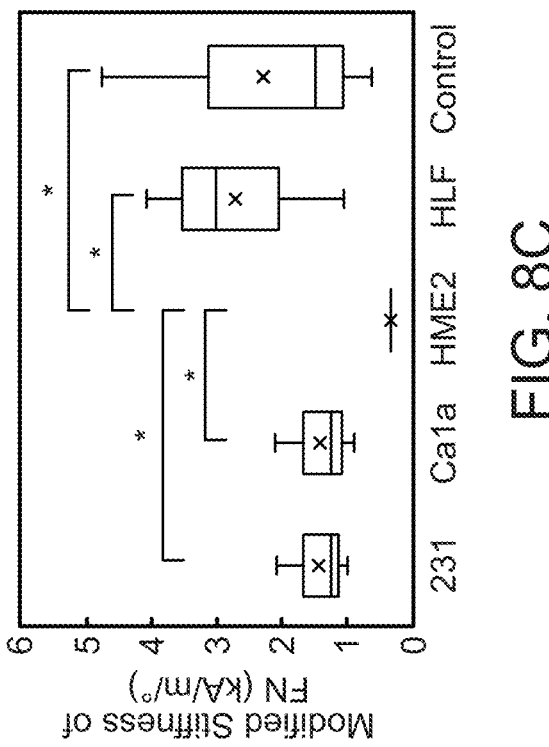
FIG. 8C shows stiffness of fibronectin band for each actuating cell line. (*=p<0.05, n=3).

Matrix breakdown was halted in MDA-MB-231, Ca1a, and HLF cells that underwent cyclic tensile manipulation (FIGS. 8A and 8B). The deflection angle at the highest magnetic field strength was significantly larger for static cultures with MDA-MB-231 and HLF cells (FIG. 8D). Interestingly, actuators tested from HLF cells undergoing mechanical loading were stiffer than no-cell actuating controls, indicating that they formed a stronger matrix than the initial fibronectin coating (FIG. 12). Fibroblasts are known to reorient the fibronectin matrix under mechanical stimulation, creating an organized and aligned fibrillar structure. This anisotropic organization likely strengthened the fibronectin in the direction of the strain. Of note, the HME2 cells were unaffected by the mechanical stimulation, achieving almost complete degradation of the fibronectin in both static and actuating conditions (FIGS. 8A-8D) To compare FN integrity between actuated cell lines a modified stiffness of the FN was calculated by imposing a slope on each of the deflection tests. The stiffness of the fibronectin in the actuating groups was significantly higher in all of the other cell lines as compared to the HME2 groups, and the stiffness of the other three cell lines were not significantly different than the no-cell control (FIG. 8C). The matrix breakdown was also only halted in the MDA-MB-231, Ca1a, and HLF cells in the high strain (20-25%) cases (FIG. 12).

Discussion

To date, the majority of studies exploring mechanotransduction and YAP/TAZ activation have solely investigated healthy cells. Wang et al. showed that cyclic stretching of smooth muscle cells on Matrigel-coated silicone chambers (0.5 Hz, 13% strain) for 24 h markedly increased YAP/TAZ expression and proliferation rates. Y. Wang, W. Cao, J. Cui, Y. Yu, Y. Zhao, J. Shi, J. Wu, Z. Xia, B. Yu, J. Liu, Arterial Wall Stress Induces Phenotypic Switching of Arterial Smooth Muscle Cells in Vascular Remodeling by Activating the YAP/TAZ Signaling Pathway, Cell Physiol Biochem 51(2) (2018) 842-853, incorporated herein by reference. Cui et al. also showed that proliferation rates were significantly reduced in primary fibroblasts cultured on a soft substrate as compared to PDMS pillars, but that the growth rate was recovered under dynamic stretching (0.1 Hz, 5% strain). Y. Cui, F. M. Hameed, B. Yang, K. Lee, C. Q. Pan, S. Park, M. Sheetz, Cyclic stretching of soft substrates induces spreading and growth, Nat Commun 6 (2015) 6333, incorporated herein by reference. However, it is known that tumorigenic cells typically natively display heightened YAP/TAZ expression and increased proliferation rates. Therefore, mechanical loading of these cancerous cells does not seem to induce the same effects. Instead, it was found that cyclic strain significantly inhibited proliferation in all three breast cancer cell lines, with clear differences seen after just 2 d in culture (~1.5 d actuation) for some cell types. Because EdU is incorporated when cells enter S phase, it appears that that mechanical stimulation does not slow the length of time it takes a cell to enter the S phase, but prolongs the length of the S, G2, or M phases. It has been shown that DNA replication can be slowed by an intra-S checkpoint in response to DNA damage. Gudipaty et al. found that stretching triggered non-cancerous cells paused in early G2 to be driven into mitosis. S. A. Gudipaty, J. Lindblom, P. D. Loftus, M. J. Redd, K. Edes, C. F. Davey, V. Krishnegowda, J. Rosenblatt, Mechanical stretch triggers rapid epithelial cell division through Piezol, Nature 543(7643) (2017) 118-121, incorporated herein by reference. Consistent with the opposite results seen by stretching tumorigenic cells, actuation may have forced the 231, Ca1a, and HME2 cells to pause in G2. Cancer cells have been successfully trapped in S/G2 previously by recombinant methioninase treatment, but further cell cycle analysis will be crucial in understanding the delayed proliferation due to mechanical stretching.

A reduction in YAP activation in two of the breast cancer cell lines after 24 h of stretching was found. Interestingly, these early studies suggest that the stretching did not induce apoptosis, which has been reported in healthy cells under mechanical loading or YAP/TAZ inactivation. This may be due to cancer cells' already enhanced ability to resist apoptosis, such that they are instead pushed into a state of quiescence or dormancy. In addition, the PDMS actuator body and the fibronectin fibrils are both markedly stiffer than the hydrogels typically utilized in mechanical loading studies. This difference may explain why static HLF cells also displayed high levels of YAP nuclearization and thus why mechanical stimulation did not cause an increase in YAP activation typically reported in the field. Yadav et al. also noted apoptosis of breast cancer cells after 4 h of cyclic stretching. However, as this was performed on a 2D synthetic substrate, it is possible that the 3D fibronectin environment partially protected the cells, reducing proliferation but not inducing apoptosis.

Lastly, while cyclic strain affected the proliferation rates of all three breast cancer cells, fibronectin matrix breakdown was not inhibited in the HME2 cells. This suggests a varied response to cyclic loading among breast cancer cell types. This difference may be dependent on the metastatic potential of the cells or their phenotype. Although Ca1a cells are initially epithelial, they are quite plastic and can undergo epithelial-mesenchymal transition (EMT). This plasticity enables relatively efficient completion of the metastatic cascade to form macrometastases in a way that is unseen in HME2 cells. It has been shown that fibronectin stabilizes the mesenchymal phenotype and that soluble fibronectin can induce Ca1a cells to a more mesenchymal phenotype. It is possible that Ca1a cells cultured on the fibronectin fibrils achieved a semi-mesenchymal state and that the inhibition of matrix breakdown is phenotypic-dependent in which there is no effect on non-plastic epithelial cells. The role of EMT and epithelial-mesenchymal plasticity (EMP) in mechanically-induced dormancy warrants further analysis and may benefit from direct comparison of paired cell phenotypes, such as the MCF10ACA1a and MCF10ACA1h breast cancer cells, on the disclosed actuation system.

It is also possible that the HME2 cells are slightly more resistant to mechanically-induced quiescence than the other two breast cancer cells in a non-phenotypic manner. The resazurin levels after 6 d of culture were 3.06 and 3.11 times higher in static vs. actuating cultures for the MDA-MB-231 and Cala cells, respectively. In contrast, the HME2 cell levels were only 2.78× higher in static cultures on day 6. Although the majority of cells may have experienced strain-induced inhibition, this small portion of functionally-active cells may have significantly broken down the fibronectin matrix. Similar results are seen for all three breast cancer cells at the lower strain rate. Despite no statistically significant difference seen between the global metabolic rates in high and low strain conditions, the low strain was not sufficient to inhibit fibronectin matrix degradation for the MDA-MB-231 or Cala cells (FIG. 11B). Due to the small region of interest, it is likely that only a few cells are needed to remain functionally-active to significantly weaken the mechanical integrity of the fibronectin fibrils. The low strain (5-10%) was below this threshold of complete inactivation for all cell types, while the high strain (20-25%) was below this threshold only for the HME2 cells. This threshold is likely cell line unique as each will have a different mechano-based proliferation sensitivity and different baseline levels of matrix metallopeptidase release.

Finally, the differential moduli of the fibronectin seen in the actuating breast cancer cell groups may be a function of their morphology. The HME2 cells formed much larger clusters in both actuating and static conditions than the MDA-MB-231 and Cala cells. Assuming the same rate of degradation, this would cause very different geometries of the fibronectin band. In MDA-MB-231 and Cala cultures, any cells that remained active and released matrix metallopeptidases would cause very small holes specked throughout the entire band of fibronectin. Conversely, even if the same small proportion of HME2 cells remained active under actuation, fewer, but much larger holes would be formed in the matrix fibrils due solely to the surface area of the HME2 clusters. During the deflection analysis, these larger holes would result in weak spots in the fibronectin fibril, causing the band to break under lower cantilever deflection despite the total amount of degradation to be equivalent. Overall, further works will benefit from a larger fibronectin region of interest in the actuator design and single-cell analysis of specific dormancy markers. The larger region of interest will also aid future cluster distribution analyses as the cells can be seeded less densely and thus the analysis will be less affected by the different proliferation rates of the conditions.

CONCLUSION

A device was described that can incorporate cyclic strain on a biologically-relevant 3D fibronectin culture to create a biomimetic lung model. A dramatic reduction in proliferation was demonstrated in three breast cancer cell lines that is not recapitulated in human lung fibroblasts. Moreover, the role of mechanical stimulation on YAP downregulation and matrix degradation rates in tumorigenic cells was demonstrated. This system enables high-throughput experimentation in standard culturing equipment, while utilizing a 3D physiologically-relevant environment. Importantly, the culturing on fibronectin fibrils supported by the PDMS actuator body allows for all traditional assays such as fluorometric/colorimetric metabolic activity measurements and immunofluorescent staining and imaging, which is often a challenge in other 3D platforms. These findings indicate a clear cellular response due to mechanical strain that may help the field further investigate the dynamic transition from microto macrometastases, including the dormancy and latent reactivation of disseminated breast cancer cells in metastatic niches.

Materials and Methods

Actuator Preparation 3D printed molds (Autodesk Ember, San Rafael, CA) were used to cure 10:1 PDMS formulation. The PDMS was cured in an oven for 2 h at 100° C. After curing the PDMS, the device was removed from the mold, and a 2 mm diameter, 1 mm thickness N42 NdFeB permanent magnet (KJ Magnetics, Pipersville, PA) was placed in the reservoir and then coated with PDMS. The devices were left in the oven at 70° C. for 24 h to ensure full curing of the PDMS.

The actuators were sterilized by soaking in 70% ethanol, rinsed three times with phosphate buffered saline (PBS), and left under UV in a laminar flow cabinet for 1-2 h. After sterilization, to suspend the physiological substrate on the region of interest, the actuators were placed in a 100 mg/mL solution of fibronectin suspended at the air-water interface. The actuators were rotated for 2 h on a rotisserie shaker (Barnstead Labquake, Lake Balboa, CA) and maintained at 30° C. at 8 RPM.

Actuator Characterization

To determine the static response of the PDMS actuator, it was placed along the long axis of a bespoke electromagnet (cylindrical core, 1-inch diameter and 6-inch tall with 300 turns). The actuators were posited on this electromagnet through a customized fixture to maintain the distance between the electromagnet and the permanent magnet constant at 3 mm. The electromagnet was supplied current by a DC power supply (PWS2326, OR). The magnetic flux density supplied by the electromagnet at different currents was measured via a hall probe (8010, F. W. Bell, OR). During actuation the device deflection angle was optically measured using a digital SLR camera (Canon 50D, Huntington, NY) (FIG. 12). This procedure was repeated for actuators with and without fibronectin coating. The magnetic field induced varied from 0-28 kA/m. The fibronectin strain percentage was calculated with:

$$L_F = \sqrt{(L_C\sin(\theta) - L_Y)^2 + (L_x - L_c\cos(\theta))^2}$$

$$\varepsilon = \frac{L_0 - L_f}{L_0}$$

Figure 13:
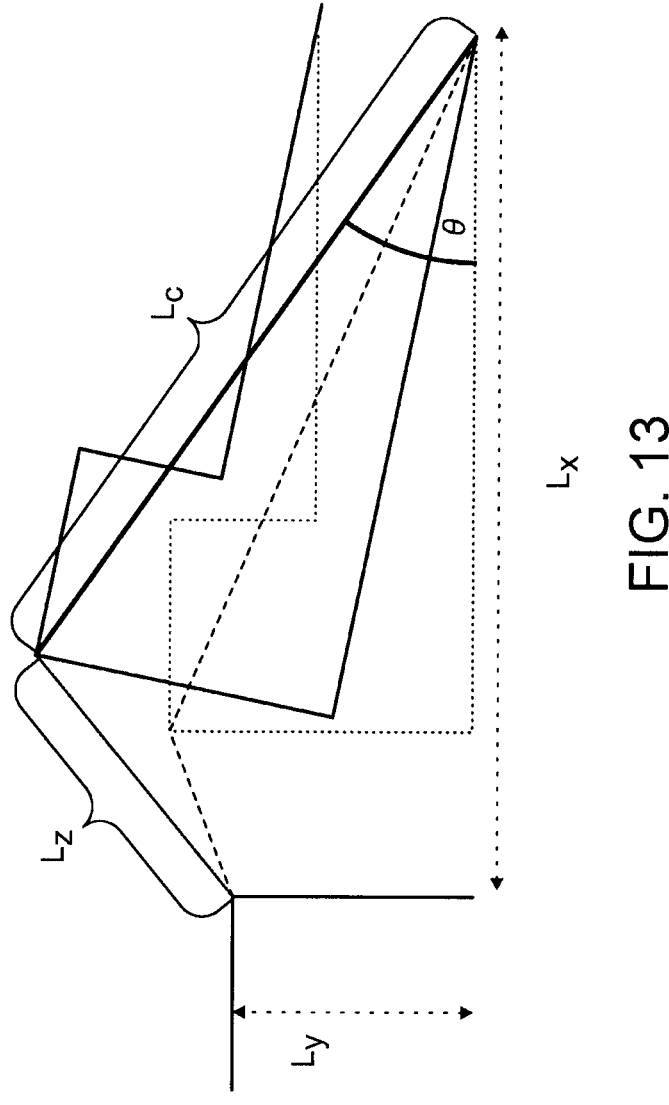
FIG. 13 illustrates the geometric model used to calculate the fibronectin strain.

FIG. 13 illustrates the geometric model used to calculate the fibronectin strain.

Magnetic Actuation Platform Fabrication & Characterization

In order to actuate the magnetic PDMS devices and overcome some of the challenges presented by other cell stretching systems, the disclosed platform was developed to easily integrate a 24-well culture plate for 3D cell study. The platform as shown in FIG. 5B consists of a linear actuator (Actuonix, Alberta, BC, Canada) programmed to move an array of permanent magnets of 19 mm in diameter and 2.4 mm thick towards a fixture suspending the multi-well culture plate. Each of the actuators is anchored by a 304 stainless steel fixture that is 12.9 mm in height with a 15.4 mm outer diameter and a 9.2 mm diameter hole through the middle to allow free deflection of the cantilever. This prevented reorientation of the actuators when exposed to the magnetic field strength in the culturing well. The stainless-steel fixture did not affect the magnetic field strength required to achieve the desired deflection angle of the cantilever.

A computational model assessed the distribution of the magnetic field in two different array configurations (FIG. 9). The most equal distribution of the magnetic field was found to be the alternating magnet array allowing for 12 permanent magnets in total. The magnetic field distribution of the permanent magnet array was determined experimentally via a hall effect described above in section 5.2. Each of the magnets on the platform was measured at 3 mm z-axis increment distances starting from the maximum travel of the linear actuator representing the closest the platform could reach the actuators. The transient magnetic field was characterized with the same instrument with experimental parameters in three regions.

Viability Studies 70,000 cells were seeded at high density (in 40-100 µl of media) onto the suspended fibronectin on the actuators in non-adherent 24-well plates. Media used was DMEM/high glucose with 10% FBS and 1% penicillin-streptomycin. The HME2 parental line additionally had 1% insulin. After 2 h, additional media was added to cover the devices (80-1000 µl). After an additional 5 h, devices were moved to new wells for metabolic testing. Upon completion, half were placed on the platform to begin cyclic actuation at 5-10% strain and 0.3 Hz. Actuating devices remained on the platform for 7 d. Control devices remained static for the same duration. A resazurin-based metabolic assay (Sigma TOX8-1KT) was performed on days 0, 2, 4, and 6. Briefly, media was removed and 1 ml of 10% resazurin stock solution (diluted in phenol-red free completed media as described above) was added to each well. After 2 h, 3 supernatant samples from each well were read using fluorescence (excitation 560 nm, emission 590 nm). The remaining solution was removed completely and replaced with completed media. The MDA-MB-231 cells were additionally assessed at 20-25% strain on days 0, 1, 3, and 5 following the same procedure. The entire media volume was collected in actuators undergoing high-strain tensile testing after 24 h of actuation (n=3 per cell type). Cells in the media were counted in triplicate using the LUNA-FL Dual Fluorescence automated cell counter (Logos Biosystems, Annadale, VA) and extrapolated to determine the percentage of cells potentially dislodged by the mechanical force (knock-off percentage).

Additional viability studies were performed on some actuators. Actuators were seeded as described above but did not undergo metabolic activity testing. The Click-iT EdU Cell Proliferation Kit for Imaging (Invitrogen) was used to detect actively dividing cells. EdU (5-ethynyl-2'-deoxyuridine) was incubated for 11 h during day 3 of actuation or static culture. Cells were fixed and the EdU reaction was completed according to manufacturer's instructions. The cell nuclei were stained using DAPI (1:500 dilution of 0.1 mg/ml stock). Separate MDA-MB-231 actuators were stained using Cellometer ViaStain AOPI staining solution (acridine orange/propidium iodide) after 7 d of high strain actuation to differentiate live and dead cells. EdU and live/dead images were taken on a Zeiss LSM 880 confocal microscope.

YAP/TAZ Analysis 18,100 cells were seeded at high density onto the suspended fibronectin on the actuators in non-adherent 24 well plates. After 1 hour, 1000 µl of media was added to each well and half were moved to the actuating platform to begin cyclic stretching. After 24 h in culture (23 h actuating for the corresponding group), actuators were fixed with 4% paraformaldehyde at 4° C., and then washed and stored in PBS. Actuators were stained using DAPI for the nucleus, phalloidin for the actin cell body (1:40 dilution), YAP (Anti-YAP in mouse, Santa Cruz H-9, 1:200 dilution), and fibronectin (Anti-fibronectin in rabbit, Sigma 3648, 1:200 dilution) and imaged on a Zeiss LSM 880 confocal microscope.

Image Quantification

LSM files were imported into MATLAB and segmented by color channel. Pixels below a certain intensity were removed as noise. This threshold was optimized per analysis and channel but remained consistent for all cell types and culturing conditions within one analysis. For proliferation analysis, the number of pixels with both green and blue in a single location was divided by the total number of blue pixels. As such, this ratio is not a direct measurement of the number of EdU positive cells but is the percentage of EdU positive pixels. This was chosen due to the confluency of the static actuators by day 3, which prevented accurate segmentation of nuclei. The analysis was performed for each tiles can image that displayed the entire fibronectin region of interest and these percentages were averaged and the standard deviation calculated and displayed.

To determine YAP colocalization, nuclei were first identified, segmented, and counted. Starting in the center of each nucleus and radiating outward, YAP stain in each pixel location was mapped to the closest nucleus that could form a continuous chain of YAP pixels. Cells were segmented when these radial projections from different cells intersected or when no YAP signal above the prescribed threshold was detected. Per each cell, the pixel intensity of the YAP channel was averaged inside the nucleus location and outside. These average intensities were then divided to determine the nuclear/cytoplasm YAP intensity ratio per cell. This was repeated for each image obtained per culturing condition, which was approximately equal to not skew sample sizes. All per-cell ratios were then averaged and the standard deviation determined per culturing condition.

Circularity was determined using a similar image processing procedure, but with respect to the yellow channel for the cell body. Each yellow pixel was mapped to a unique nucleus. When the cytoplasm of two or more cells was in contact, these cells were considered to be in a cluster. Each cluster was tagged and the size, determined by the number of unique nuclei, was noted. The perimeter and area of each unique cell was determined from the segmented yellow channel. The circularity was then calculated using the following formula $$Circularity = \frac{4\pi \cdot Area}{Perimeter^2}$$

such that the values were normalized from 0 to 1. To report the cluster results, the weighted average was taken such that the size would not be significantly skewed by lone cells amongst large networks. The weighted average was calculated such that each cell has equal contribution, instead of each cluster.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

What is claimed is:

1. A method for modeling mechanical forces on a cell culture, the method comprising:

providing a cell-culture platform comprising a magnet, a magnetically actuated cantilever, a non-magnetic frame, and an extracellular matrix (ECM) protein for culturing cells upon, wherein a first point of the ECM protein is directly contacting a fixed portion of a frame of the cell-culture platform and a second point of the ECM protein is directly contacting a magnetically actuated portion of a cantilever that is operably coupled to the cell-culture platform, wherein the cell-culture platform does not include any other deformable membrane supporting the ECM protein, wherein the ECM protein is at least one ECM protein selected from the group consisting of fibronectin, elastin, laminin, and vitronectin, and wherein the non-magnetic frame surrounds the magnetically actuated cantilever and the magnet is positioned within the magnetically actuated cantilever;

culturing cells on the ECM protein; and cyclically changing the distance between the fixed portion and the actuated portion to impart strain on the ECM protein and cells cultured thereon.

2. The method of claim 1 further comprising analyzing the cells cultured thereon after a period of cyclically changing the distance between the fixed portion and the actuated portion.

3. The method of claim 1 wherein cyclically changing the distance is performed at a frequency of between about 0.1 and about 1.0 Hz to impart strain at a strain value between about 5% and 25%.

4. The method of claim 1 wherein the ECM protein, the fixed portion, and the actuated portion are within a well of a multi-well plate.

* * * * *